US009936908B1

(12) United States Patent
Acosta et al.

(10) Patent No.: US 9,936,908 B1
(45) Date of Patent: Apr. 10, 2018

(54) IN VIVO ANALYTE DETECTION SYSTEM

(71) Applicant: Verily Life Sciences LLC, Mountain View, CA (US)

(72) Inventors: Victor Marcel Acosta, San Francisco, CA (US); Jerrod Joseph Schwartz, San Francisco, CA (US); Russell Norman Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 547 days.

(21) Appl. No.: 14/558,389

(22) Filed: Dec. 2, 2014

Related U.S. Application Data

(60) Provisional application No. 62/074,625, filed on Nov. 3, 2014.

(51) Int. Cl.
*A61B 5/00* (2006.01)
*A61B 5/1455* (2006.01)
*A61B 5/05* (2006.01)
*A61B 5/0205* (2006.01)
*A61B 5/145* (2006.01)

(52) U.S. Cl.
CPC ........ *A61B 5/14556* (2013.01); *A61B 5/0022* (2013.01); *A61B 5/02055* (2013.01); *A61B 5/0515* (2013.01); *A61B 5/14546* (2013.01); *A61B 5/4839* (2013.01); *A61B 5/681* (2013.01); *A61B 5/742* (2013.01); *A61B 5/746* (2013.01)

(58) Field of Classification Search
CPC ... A61B 5/1455; A61B 5/145; A61B 5/14546; A61B 5/14556; A61B 5/681; A61B 5/4839; A61B 5/743; A61B 5/746
See application file for complete search history.

(56) References Cited

U.S. PATENT DOCUMENTS

| 7,495,233 | B2 * | 2/2009 | Pfister | A61B 5/0059 |
| | | | | 250/458.1 |
| 2009/0192437 | A1 | 7/2009 | Soltz et al. | |
| 2014/0276356 | A1 | 9/2014 | Victor et al. | |

OTHER PUBLICATIONS

Mark Bates et al., "Multicolor Super-resolution Imaging with Photo-switchable Fluorescent Probes", Science, Sep. 21, 2007; 317(5845), pp. 1749-1953.
Sebastian van de Linde et al., "Direct stochastic optical reconstruction microscopy with standard fluorescent probes", Nature Protocols, vol. 6, No. 7, 2011, pp. 991-1009.

(Continued)

*Primary Examiner* — Eric Winakur
(74) *Attorney, Agent, or Firm* — McDonnell Boehnen Hulbert & Berghoff LLP

(57) ABSTRACT

A light source emits light into a first portion of a living body. Functionalized particles within the body are configured to specifically bind to a target analyte, and upon receiving the emitted light, undergo a reaction that separates a detectable label from the functionalized particle. A sensor device is configured to detect a response signal from a second portion of the living body that is indicative of an abundance of the detectable label in the second portion. A control system uses the sensor device to obtain sensor data indicative of the response signal from the second portion of the living body detected by the sensor device during a measurement interval, and determines a presence or absence of the target analyte within the first portion of the living body based in part on the obtained data.

18 Claims, 15 Drawing Sheets

(56) References Cited

OTHER PUBLICATIONS

Christoph Greb, "Highlighter Proteins and Fluorescent Timers: Leica Science Lab," Leica Microsystems, Jun. 20, 2012, pp. 1-6.
Graham T. Dempsey et al., "Photoswitching Mechanism of Cyanine Dyes", J. Am. Chem. Soc., 2009, vol. 131, No. 51, pp. 18192-18193.

* cited by examiner

IN VIVO ANALYTE DETECTION SYSTEM

CROSS-REFERENCE TO RELATED APPLICATIONS

This application claims priority to U.S. Provisional Patent Application No. 62/074,625, filed Nov. 3, 2014, which is incorporated herein by reference in its entirety and for all purposes.

BACKGROUND

Unless otherwise indicated herein, the materials described in this section are not prior art to the claims in this application and are not admitted to be prior art by inclusion in this section.

A number of diagnostic methods have been developed to evaluate physiological conditions of a person by detecting and/or measuring one or more analytes in a person's blood or other bodily fluids or tissues. The one or more target analytes could be any analytes that, when present in or absent from the blood, or present at a particular concentration or range of concentrations, may be indicative of a medical condition or health state of the person. The one or more target analytes could include enzymes, reagents, hormones, proteins, cells or other molecules, such as carbohydrates, e.g., glucose.

SUMMARY

A light source emits light into a first portion of a living body. Functionalized particles within the body are configured to specifically bind to a target analyte, and upon receiving the emitted light, undergo a reaction that separates a detectable label from the functionalized particle. A sensor device is configured to detect a response signal from a second portion of the living body that is indicative of an abundance of the detectable label in the second portion. A control system uses the sensor device to obtain sensor data indicative of the response signal from the second portion of the living body detected by the sensor device during a measurement interval, and determines a presence or absence of the target analyte within the first portion of the living body based in part on the obtained data.

Some embodiments of the present disclosure provide a system. The system can include a light source, a sensor device, and a control system. The light source can be configured to emit light into a first portion of a living body that has received a plurality of functionalized particles. The emitted light can include light at a first wavelength. The functionalized particles can each include a first portion coupled to a second portion via a photocleavable linker. The first portion can include a detectable label. The second portion can be configured to specifically bind to a target analyte. The photocleavable linker can be configured to undergo a reaction that separates the first portion from the second portion responsive to absorption of light at the first wavelength. The sensor device can be configured to detect a response signal from a second portion of the living body. The response signal can be indicative of an abundance of the detectable label in the second portion of the living body. The control system can be configured to: (i) following an emission by the light source of light at the first wavelength into the first portion of the living body, use the sensor device to obtain sensor data indicative of the response signal from the second portion of the living body detected by the sensor device during a measurement interval, and (ii) determine a presence or absence of the target analyte within the first portion of the living body based in part on the obtained sensor data.

Some embodiments of the present disclosure provide a method. The method can include introducing a plurality of functionalized particles into a living body. The functionalized particles can each include a first portion coupled to a second portion via a photocleavable linker. The first portion can include a detectable label. The second portion can be configured to specifically bind to a target analyte. The photocleavable linker can be configured to undergo a reaction that separates the first portion from the second portion responsive to absorption of light at a first wavelength. The method can also include emitting light into a first portion of the living body via a light source. The emitted light can include light at the first wavelength. The method can also include using a sensor device to obtain sensor data following emitting the light. The sensor data can be indicative of a response signal from a second portion of the living body detected by the sensor device during a measurement interval. The response signal can be indicative of an abundance of the detectable label in the second portion of the living body. The method can also include determining a presence or absence of the target analyte within the first portion of the living body based in part on the obtained data.

Some embodiments of the present disclosure also provide a drug-delivery system. The drug-delivery system can include one or more light sources, a sensor device, and a control system. The one or more light sources can be configured to emit light into a first portion of a living body. The emitted light can include light at a first wavelength and light at a second wavelength. The living body may have received a plurality of functionalized particles. The functionalized particles can each include a first portion coupled to a second portion via a photocleavable linker. The first portion can include a detectable label. The second portion can include an agent configured to transition from a biologically inactive state to a biologically active state responsive to absorption of light at the first wavelength. The photocleavable linker can be configured to undergo a reaction that separates the first portion from the second portion responsive to absorption of light at the second wavelength. The sensor device can be configured to detect a response signal from a second portion of the living body. The response signal can be indicative of an abundance of the detectable label in the second portion of the living body. The control system can be configured to: (i) following an emission by the one or more light sources of light at the first wavelength into the first portion of the living body, use the sensor device to obtain sensor data indicative of the response signal from the second portion of the living body detected by the sensor device during a measurement interval, and (ii) determine an abundance of the agent that transitioned to the biologically active state at the first portion of the living body based in part on the obtained sensor data.

Some embodiments of the present disclosure provide means for introducing a plurality of functionalized particles into a living body. The functionalized particles can each include a first portion coupled to a second portion via a photocleavable linker. The first portion can include a detectable label. The second portion can be configured to specifically bind to a target analyte. The photocleavable linker can be configured to undergo a reaction that separates the first portion from the second portion responsive to absorption of light at a first wavelength. Some embodiments of the present disclosure can also include emitting light into a first portion of the living body via a light source. The emitted light can include light at a first wavelength. Some embodiments of the present disclosure can also include using a sensor device to obtain sensor data following emitting the light. The sensor data can be indicative of a response signal from a second portion of the living body detected by the sensor device during a measurement interval. The response signal can be indicative of an abundance of the detectable label in the second portion of the living body. Some embodiments of the present disclosure can also include determining a presence or absence of the target analyte within the first portion of the living body based in part on the obtained data.

These as well as other aspects, advantages, and alternatives, will become apparent to those of ordinary skill in the art by reading the following detailed description, with reference where appropriate to the accompanying drawings.

DETAILED DESCRIPTION

Figure 1A:
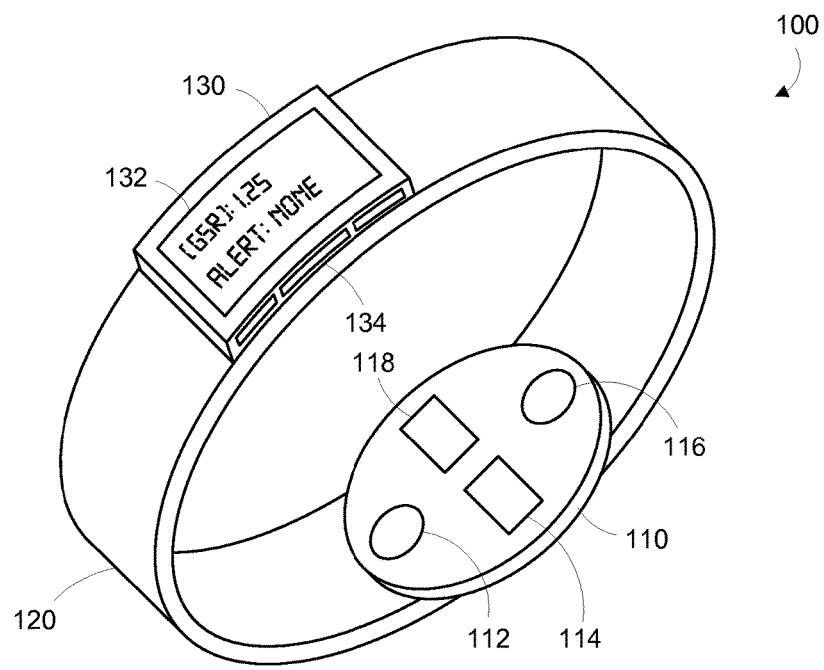
FIG. 1A is a perspective view of an example wearable sensor device.

In the following detailed description, reference is made to the accompanying figures, which form a part hereof. In the figures, similar symbols typically identify similar components, unless context dictates otherwise. The embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where activity of functionalized particles in one area is monitored using measurements detected from another area. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vivo applications are possible as well. Accordingly, the environment may also include a test tube or other vessel for holding a fluid.

I. Overview

A diagnostic system can non-invasively detect and measure a plurality of physiological parameters of a person, which can include any parameters that may relate to the person's health. For example, the system could include sensors for measuring blood pressure, pulse rate, skin temperature, etc. At least some of the physiological parameters may be obtained by the system non-invasively detecting and/or measuring one or more analytes in blood circulating in subsurface vasculature. The system can measure any analytes that, when present in or absent from the blood, or present at a particular concentration or range of concentrations, may be indicative of a medical condition or health of the person. For example, the one or more analytes could include enzymes, hormones, proteins, cells or other molecules.

The system can be used to obtain health-related information by detecting response signals from particles within the body using a sensor device arranged exterior to the body. The particles may be microparticles or nanoparticles introduced into the circulatory system of the body. The particles can be functionalized by covalently or otherwise attaching or associating various functional groups to perform particular operations within the body. Generally, the systems described herein include particles with at least one component that can be detected in vivo using a sensor exterior to the device, such as a detectable label, that is coupled to another functional component, such as an analyte-selective binder or a biologically inactive agent, through a photocleavable linker. Photocleaving light emitted into the body can be absorbed by the photocleavable linker, which causes the photocleavable linker to undergo a reaction that separates the detectable label from the other functional component, at which point the detectable label may disperse through the circulatory system separate from the other functional component. The detectable label may be detected using a sensor exterior the body that emits an interrogation signal into the body, and then detects a response signal from the detectable label. For example, the detectable label may be a fluorophore that fluoresces in response to absorbing light at an excitation wavelength.

With such particles, applying photocleaving light into a region of the body can be used to query activity of the functionalized particles in that region. More particularly, activity (or at least presence) of the functionalized particles in one region can be inferred from measurements of another region of the body. For example, a wrist-mounted sensor device may be configured to detect response signals from a detectable label in the wrist or forearm of the body. After introducing functionalized particles into the body and allowing them to disperse, photocleaving light may be emitted into the shoulder of the body. The application of the photocleaving light cleaves the detectable label from the functionalized particles in the shoulder, and the cleaved detectable labels can disperse through the circulatory system where they may be detected by the wrist-mounted sensor device.

The measurements from the wrist-mounted device may be used to determine different clinically-relevant properties about the shoulder depending on the nature of the functionalized particles used. In an example in which the functionalized particles are configured to specifically bind to a particular clinically-relevant analyte, measurements from the wrist-mounted sensor device may be used to determine whether the analyte is present in the shoulder. In an example in which the functionalized particle includes a biological agent, such as a drug or a molecular payload, measurements from the wrist-mounted sensor device may be used to determine a dosage of the biological agent delivered at the shoulder. Further, the biological agent may transitions from a biologically inactive state to a biologically active state in response to a stimulus. A drug-activation stimulus may be applied to the same region that the cleaving light is applied. Thus, measurements from the wrist-mounted sensor device may be used to determine a dosage of the biological agent delivered and/or activated at the shoulder To increase sensitivity of the system, the detectable labels may be configured to modify their response signal upon absorbing a particular stimulus, such as a fluorophore that transitions from a low fluorescence state to a high fluorescence state upon receiving a stimulus, or a fluorophore that transitions from a first fluorescence state to a second fluorescence state upon receiving a stimulus. Thus, in addition to applying photocleaving light to a particular location of the body, the systems may also apply a photoactivating light and/or photoswitching light. The cleaved detectable labels (i.e., those that received both the photocleaving light and the photoactivating or photoswitching light) can then exhibit a response signal that is differentiated from detectable labels that have not been cleaved. Further, the sensor device can be configured such that sensor data generated by the sensor device differentiates between the two response signals.

Generally, measurements from the sensor device are obtained during a measurement interval that follows application of the photocleaving light. The measurements are used as a basis to determine whether the measurements indicate an increase or modification in the response signals detected during the measurement interval that is consistent with a group of functionalized particles being cleaved at another location of the body and dispersed through the circulatory system during the measurement interval.

The above described system may be implemented as a wearable sensor device for obtaining measurements from a first location on a body and a light source for emitting light into other locations of the body. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The detector, modulation source, interrogation signal source (if applicable) and, in some examples, the processor, may be provided on the wearable device. In other embodiments, the above described system may be implemented as a stationary measurement device to which a user must be brought into contact or proximity with or as a device that may be temporarily placed or held against a body surface during one or more measurement periods.

The above-described system may additionally or alternatively be implemented as a portable sensor device, such as a wand or other handheld apparatus that includes both a light source for emitting light into the body and a sensor system for obtaining measurements from the body. The portable sensor device may be moved around the body and positioned along or proximate to an exterior surface of the body. In some examples, the portable sensor device may further be configured for insertion within a body cavity for obtaining measurements from locations of the body most readily accessible inside the cavity.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Example Sensor Devices

Some examples of the present disclosure relate to sensor devices that are configured to be worn on a living body and used to obtain measurements related to physiological conditions of the body via sensors on the devices. Such devices, described herein as wearable devices, can be configured to be mounted to an external body surface of a wearer and to enable a variety of applications and functions. The term "wearable device," as used in this disclosure, refers to any device that is capable of being worn at, on or in proximity to a body surface, such as a wrist, ankle, waist, chest, or other body part. Such wearable devices include a housing (i.e., a rigid or semi-rigid enclosure) and a mount configured to mount a contact surface of the housing to the external body surface of the wearer. A sensor disposed on a portion of the contact surface can detect one or more properties of the body of the wearer when the contact surface is mounted to the external body surface. Such wearable devices could enable a variety of applications, including measuring physiological information about a wearer, indicating such measured physiological information or other information to the wearer (e.g., using a haptic feedback system, a display system, an audio feedback system, a communication to a server that is configured to generate an indication to the wearer), or other user interface systems.

An example wearable device can automatically measure multiple physiological parameters of a person wearing the device via sensors included in the device. In order to take in vivo measurements in a non-invasive manner from outside of the body, the wearable device 100 may be positioned on a portion of the body where subsurface vasculature or other elements of the body of the wearer may be detected, which depends in part on the type of detection system used and its sensitivity. The wearable device may be placed in close proximity to the skin or tissue. Depending on the mounting location of the device, the device may accordingly be implemented in a variety of different form factors that are configured to be mounted to a variety of different body surfaces. In some embodiments, sensor devices involved in applications described herein may be portable devices (e.g., handheld devices) that are configured to be positioned such that a sensor area of the device is in proximity to an exterior body surface (e.g., a wand instrument with a handle) and/or inserted into a cavity of the body.

Examples of wrist-mountable devices are shown in FIGS. 1A-1B, 2A-2B, 3A-3B, 4A-4B, and 5A-5B. While various features of wearable devices are described in connection with each of these figures, by way of example, it is noted that each of these features may be implemented by sensor devices that are not wearable, such as portable and/or handheld sensor devices. As shown in FIG. 1A, the example wrist-mounted device 100 includes a sensor housing 110, a user interface module 130, and mounting band 120. The sensor housing 110 and/or user interface module 130 also includes a variety of electronic modules, such as a power system, and one or more sensors.

A. Housing

Figure 1B:
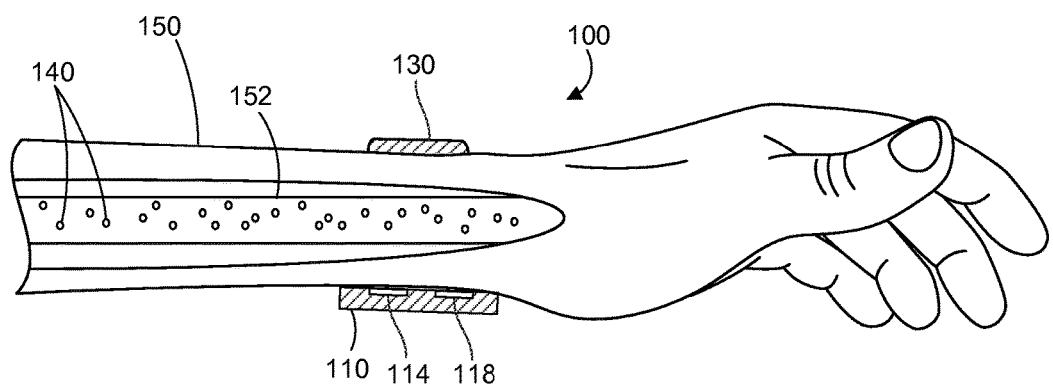
FIG. 1B is a partial cross-sectional view of an example wearable sensor, while mounted on a human wrist.

The sensor housing 110 is disposed on the mount 120 to facilitate contact between the body surface and the sensor housing 110 when the device 100 is worn. For instance, FIG. 1B shows the example device 100 in a side cross-sectional view when the device 100 is mounted to a wrist. As shown in FIG. 1B, the sensor housing 110 is situated over the body surface (e.g., the anterior side, or palmar side, of the wrist above the ulnar artery).

Alternatively, the sensor devices described herein may be implemented in a portable form factor that is not configured to be mounted to a body. For example, the sensor devices described herein may be implemented as a wand instrument, or another handheld or portable device that can be manually or robotically positioned in proximity to various locations of the body. A portion of such a handheld device in which sensor(s) are mounted can then be positioned along or near the exterior of a body at various locations. A housing of such a handheld device may optionally include a partially flexible (e.g., conformable) surface that adapts to various locations of the body. In some cases, the housing of such a device may be configured to be inserted into various cavities of the body, such as a rectal, vaginal, or esophageal probe to allow for obtaining measurements from locations within such cavities.

B. User Interface

The wearable device 100 may also include a user interface 130. Using the user interface 130, the wearer of the device may receive outputs and provide inputs to the device 100. Outputs may include, for example, recommendations or alerts based on physiological measurements obtained using the wearable device and/or other information related to the device, such as battery condition or status information. Inputs may include adjustments to settings on the device (e.g., measurement interval, data reporting format, etc.). As shown in FIG. 1A, the user interface 130 can include a display 132 for providing outputs, and buttons 134 for receiving user inputs. As shown in FIG. 1A, the display 132 can be used to render messages to be read by the wearer, such as text that indicates a measure of Galvanic skin resistance (GSR). The display could also be used to display alerts to the user. The user interface 130 may include a variety of other components to provide and/or receive information via visual component(s) (e.g., a display and/or a camera), auditory component(s) (e.g., an audio loudspeaker and/or a microphone), and/or tactile component(s) (e.g., a vibration transducer and/or an accelerometer).

In some examples, the user interface 130 may additionally or alternatively be implemented via communication between the wearable device 100 and other device(s). For instance, a wearer may receive outputs (e.g., alerts) via their cell phone, computer, or other device. The wearer may also provide inputs (e.g., to adjust settings of the device) via such other device. Accordingly, the wearable device 100 can be configured to communicate with such other devices via wireless signals, for example. In addition, the wearable device 100 may communicate with other devices, which may be used to store and/or process data related to the physiological measurements alone or in coordination with the processing performed locally by the device 100. For instance, a communicatively coupled computing system may receive data indicating measurements from the wearable device 100, and analyze those measurements to determine a health state of the wearer. Such a computing system may also store indications of wearer-associated measurements and/or health states over time, and generate reports from that information.

C. Mount

The mounting band 120 can be used to mount the device 100 at, on or in proximity to the body surface. The mount 120 may prevent the wearable device 100 from moving relative to the body to reduce measurement error and noise. In one example, as shown in FIG. 1A, the mount 120 may take the form of a strap or band that can be worn around a part of the body, such as a wrist, ankle, arm, leg, waist, and/or chest. In some examples, the device 100 may additionally or alternatively include an adhesive substrate for mounting the wearable device 100 to a body surface.

Figure 2A:
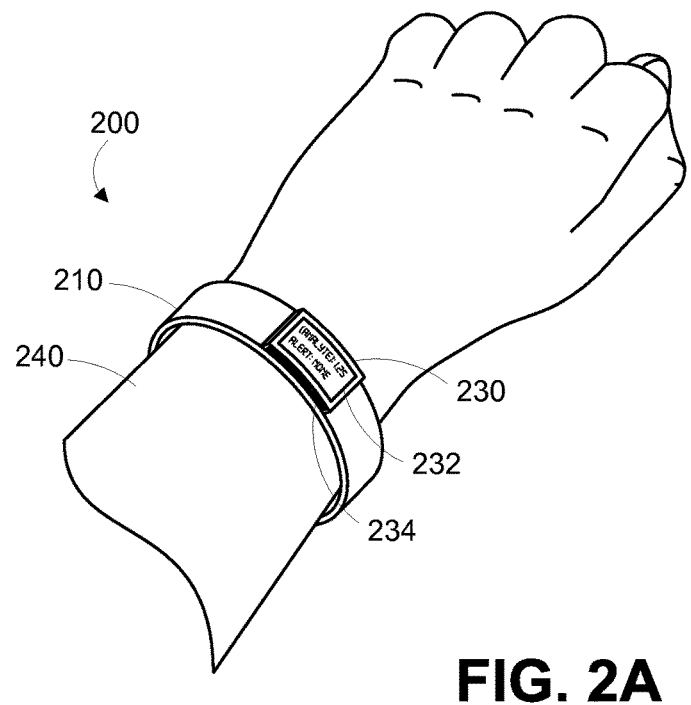
FIG. 2A is a perspective top view of an example wrist-mounted device, when mounted on a wearer's wrist.
Figure 2B:
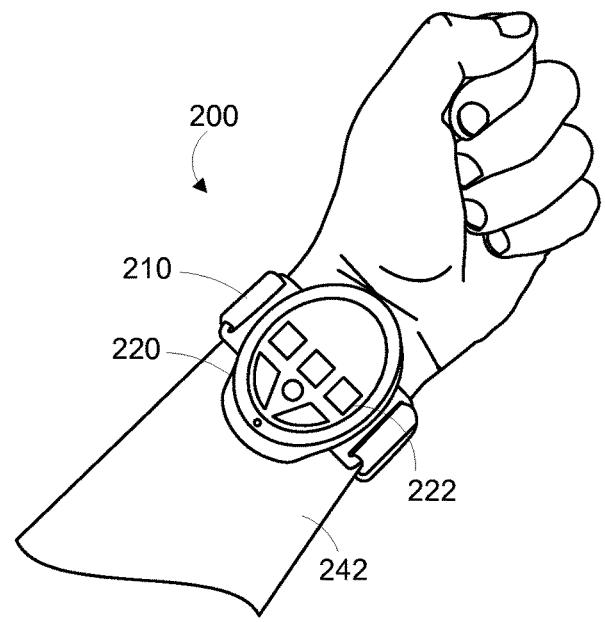
FIG. 2B is a perspective bottom view of an example wrist-mounted device shown in FIG. 2A, when mounted on a wearer's wrist.

In some implementations, the body-mountable device 100 may be a wrist-mounted device. An example wrist-mounted device 200 is shown in FIGS. 2A and 2B. The wrist-mounted device 200 may be mounted to the wrist, similar to a watch or bracelet. FIG. 2A is a top view of the example wrist-mounted device 200 worn on a wrist. FIG. 2B is a reverse view of the example wrist-mounted device 200 shown in FIG. 2A. FIGS. 2A and 2B show opposing views of the wrist-mounted device 200 being worn on the wrist. FIG. 2A shows a perspective in which a posterior side 240 of the wrist is visible; FIG. 2B shows a perspective in which an anterior side 242 of the wrist is visible.

The wrist mounted device 200 can include a wristband 210, a sensor housing 220, and a user interface 230. As shown in FIGS. 2A and 2B, when the device 200 is mounted to the wrist, the sensor housing 220 can be positioned over the anterior side 242 of the wearer's wrist, and the user interface 230 can be positioned on the posterior side 240 of the wearer's wrist. The wearer of the device 200 may receive, via the user interface 230, one or more recommendations or alerts related to physiological measurements obtained using the wrist-mounted device 200. Such a configuration may be perceived as natural for the wearer of the device 200 in that it is common for the posterior side 240 of the wrist to be observed, such as during the act of checking a wrist-watch. Accordingly, the wearer may easily view a display 232 of the user interface 230. Further, the sensor housing 220 may be located on the anterior side 242 of the wearer's wrist where the subsurface vasculature or other elements of the wearer's body (e.g., carpal tunnel, ulnar artery, etc.) may be readily observable via physiological sensors mounted on and/or within the sensor housing 220. However, other implementations may have other configurations.

The display 232 may be configured to display a visual indication of an alert, recommendation, and/or an indication of the measured physiological parameters, for instance, the presence or concentrations of certain blood analytes being measured, a pulse rate, an oximetry measurement, etc. Further, the user interface 230 may include one or more buttons 234 for accepting inputs from the wearer. Additionally or alternatively, the sensor housing 220 may also include one or more buttons 222 for accepting inputs from the wearer. The user inputs may be used to adjust settings of the wearable device 200, such as user interface settings (e.g., the manner of displaying information on the display 232), aspects of the data collection system (e.g., measurement intervals, initiation of measurement, communication settings, other aspects related to the functioning of the device 200, and/or or indications of the wearer's current health state (e.g., normal, migraine, shortness of breath, heart attack, fever, "flu-like" symptoms, food poisoning, etc.).

Figure 3B:
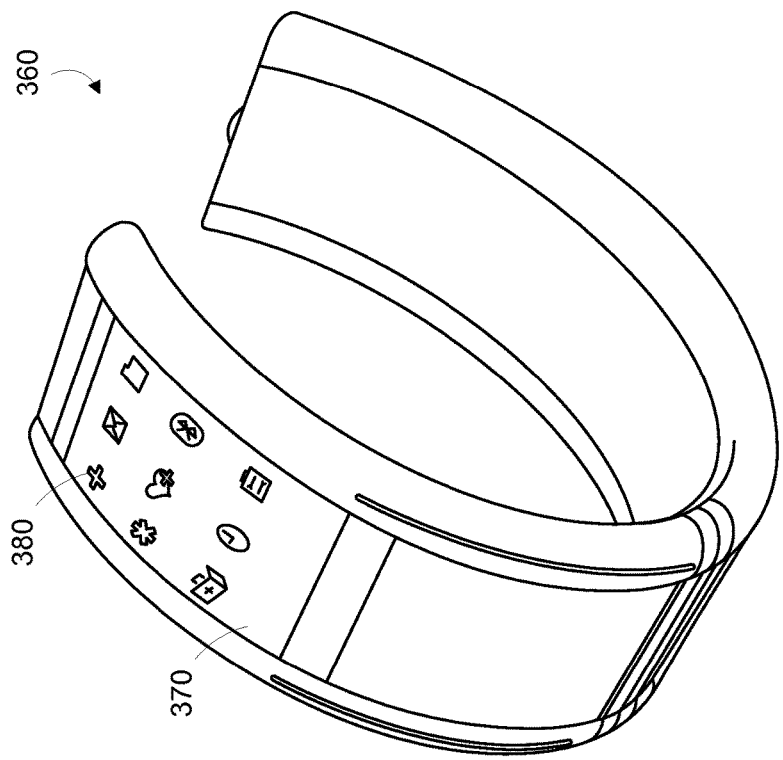
FIGS. 3A and 3B are perspective views of other example wrist-mounted devices.
Figure 3A:
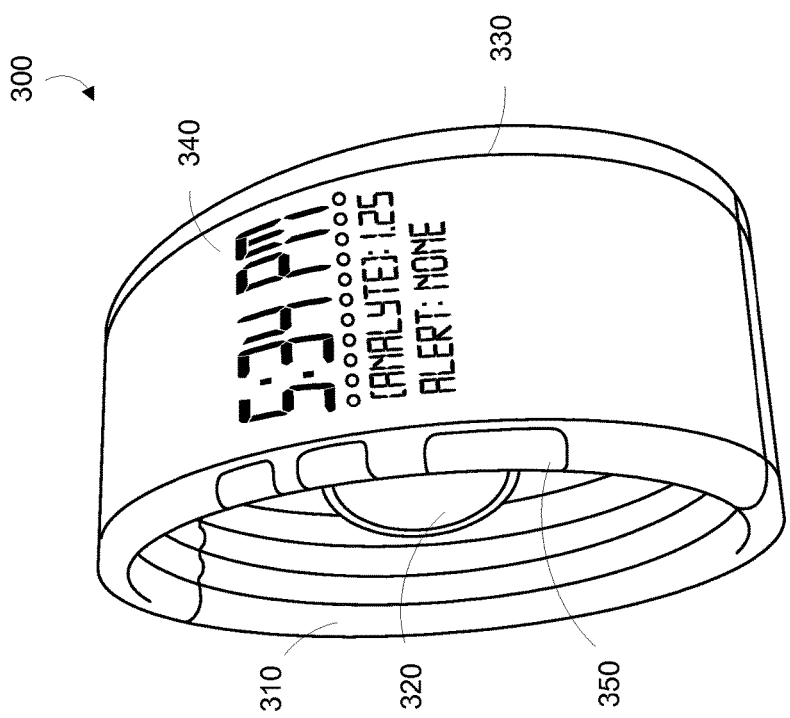

FIGS. 3A and 3B illustrate additional examples of wrist-mountable wearable sensor devices 300, 360. As shown in FIG. 3A, a wrist-mountable device 300 may be provided on a cuff 310. Similar to the previously discussed embodiments, device 300 includes a measurement platform 320 and a user interface 330, which may include a display 340 and one or more buttons 350. The display 340 may further be a touch-screen display configured to accept one or more input by the wearer. An example device that includes a touch-screen display is shown in FIG. 3B. As shown in FIG. 3B, display 370 may be a touch-screen configured to display one or more virtual buttons 380 for accepting one or more inputs for controlling certain functions or aspects of the device 360, or inputs of information by the user, such as current health state. Other examples are also possible.

D. Power System

The wearable device 100 additionally includes a power system for providing power to the electronics of the device 100. The device 100 may include various electronics configured to operate the sensor(s), user interface(s), communication system(s), and/or other electronic features described in connection with operation of the wearable device 100. The electronics may include, for example, a microprocessor that is configured to execute program instructions stored on a data storage situated within the device 100.

In some examples, the wearable device 100 may include one or more circuit boards within the sensor housing 110, and various electronics could be disposed on the circuit board(s). Additionally, the device 100 can include an energy storage device, such as a rechargeable battery, which is electrically coupled to the circuit board and configured to provide power to the electronics. The power system of the device 100 can therefore include circuits configured to regulate and/or control charging of the battery, and to supply the remaining electronics with power using energy discharged from the battery. Charging the battery may involve providing energy to the device 100 via a conductive coil that receives time-variant magnetic flux from a wireless charging system to induce voltage across the coil. The voltage variations on the coil could be rectified and/or regulated and used to apply a charging current to the battery. Charging may also involve providing energy to the device 100 via a charging port with conductive terminals configured to receive a connector. Energy received at the conductive terminals could be used to apply a charging current to the battery.

E. Sensor(s)

The sensor housing 110 may include at least one sensor for detecting at least one physiological property of the body of the wearer, which could include any parameters that may relate to the health of the person wearing the wearable device. For example, the sensor housing 110 can include a pulse rate sensor and/or pulse oximetry sensor having two light-sensitive elements 112, 116, and a light emitter 114. While the device 100 is mounted over a wrist (as in FIG. 1B), the light emitter 114 can emit light into the body tissue. Some of the emitted light is then reflected by the tissue and received by the light-sensitive elements 112, 116. The tissue of the arm 150 includes a variety of materials with different degrees of reflectivity, such as skin, muscle, bone, connective tissues, vasculature 152, etc., and so the intensity of reflected light during a given measurement depends on the composition of the tissue over the sensor. Over timescales of a few seconds the tissue composition remains fairly constant with the exception of arterial blood that traverses the vasculature 152 in a non-continuous, pulsing manner related to the wearer's heartbeat. Intensity modulations in the reflected light can be attributed to the pulsing blood in the vasculature 152 (e.g., through the ulnar artery), and so the frequency of such intensity modulations can be used to determine the wearer's pulse rate.

Other sensors may additionally or alternatively be included in the sensor housing 110. The sensor housing 110 could include sensors mounted thereon for measuring blood pressure, galvanic skin response, skin temperature, analyte levels, etc. In some examples, at least one of detector in the sensor housing 110 is configured to non-invasively measure one or more analytes in blood circulating in subsurface vasculature 152 proximate to the wearable device 100. In a non-exhaustive list, the sensor housing 110 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. For instance, the sensor housing 130 could include a sensor configured to detect a Galvanic skin resistance (GSR) of skin at the external body surface of the wearer by applying an electric potential between two probes in electrical contact with skin at the external body surface of the wearer.

i. Functionalized Particles

Additionally or alternatively, the body of the wearer (e.g., the subsurface vasculature 152) could include artificial or other contrast agents (e.g., fluorophores, fluorescent nanodiamonds, chromophores, acoustic particles, magnetic particles) functionalized or otherwise configured to enable the detection of one or more properties of the body of the wearer using a sensor mounted to the sensor housing 110. For example, a contrast agent including a fluorophore could be configured to selectively bind to an analyte of interest in the blood of the wearer, and a sensor could be operated to determine a presence, location, binding state, or other properties of the contrast agent in the blood. In another example, the contrast agent may include a magnetic and/or paramagnetic material that can be detected via magnetic interaction with an external magnetic field (e.g., using a probing magnetic field and/or magnetometer). The determined one or more properties of the contrast agent could be used to determine the presence or concentration of the analyte in the blood of the wearer. Other contrast agents, properties of the body of the wearer, and configurations are anticipated.

The functionalized particles 140 may be configured to bind to a clinically-relevant analyte with a predetermined binding affinity and/or selectivity. For example, the functionalized particles may include aptamer-particle conjugates in which the aptamer is configured to bind to the clinically-relevant analyte. Other analyte-selective binders may also be used (e.g., antibodies). The term "bind" is understood in its broadest sense to also include any detectable interaction between the clinically relevant analyte and the functionalized particles. The wearable sensor device can be used to obtain sensor data of a response signal from the functionalized particles, and a determination of the presence, absence and/or a concentration of the clinically-relevant analyte can be made based on the response signal.

The functionalized particles 140 may also include a magnetic and/or paramagnetic material, and the wearable device may detect the presence, absence, and/or concentration of the particles based on a magnetic interaction with the particles. Moreover, the sensor device may direct a magnetic field into the portion of subsurface vasculature to cause the functionalized particles to collect in a lumen of the portion of subsurface vasculature, and thereby enhance the measurements made using the sensor device.

ii. Interrogating and Response Signals

In some examples, the wearable device 100 may transmit an interrogating signal into the subsurface vasculature 152 via a signal source 118, and then detect a response signal. The response signal may be fluorescence emitted by a fluorophore of interest, and the interrogating signal may be light that excites the fluorophore. The response signal may be a magnetic signature indicative of a magnetic or paramagnetic material present within the first portion of the body, and the interrogating signal may be application of a probing magnetic field. The response signal may be related to binding of a clinically-relevant analyte to functionalized particles that can be detected using the sensor device, e.g., aptamer-particle conjugates, present in a lumen of the subsurface vasculature 152.

The signal source 118 is configured to transmit an interrogating signal that can penetrate the wearer's skin into the subsurface vasculature 152. For example, the interrogating signal may be configured to energize (or otherwise interact with) functionalized particles within a lumen of the subsurface vasculature 152. The interrogating signal can be any kind of signal that is benign to the wearer, such as electromagnetic, magnetic, optic, acoustic, thermal, mechanical, and results in a response signal that can be used to measure a physiological parameter. For instance, the response signal may be indicative of binding between the clinically-relevant analyte to the functionalized particle(s) circulating within the subsurface vasculature 152.

In some examples, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, be near infrared radiation having a wavelength between about 700 nanometers and about 900 nanometers. In some examples, the functionalized particles 140 include a fluorophore. The interrogating signal may therefore be an electromagnetic radiation signal with a wavelength that can excite the fluorophore and penetrate the skin or other tissue and subsurface vasculature 152 (e.g., a wavelength in the range of about 700 to about 900 nanometers), and the response signal may be fluorescence radiation from the fluorophore that can penetrate the subsurface vasculature and tissue to reach the detector.

In some cases, an interrogating signal is not necessary to measure one or more of the physiological parameters and, therefore, the wearable device 100 may omit the signal source 118. For example, functionalized particles may include an autofluorescent or luminescent marker, such as a fluorophore, that will automatically emit a response signal indicative of the binding of the clinically-relevant analyte to the functionalized particles 140, without the need for an interrogating signal or other external stimulus. In some examples, the functionalized particles 140 may include a chemiluminescent marker configured to produce a response signal in the form of luminescence radiation produced in response to a chemical reaction initiated, at least in part, to the binding of the target analyte with the particle.

A collection magnet may also be included in the sensor housing 110. In such embodiments, the functionalized particles may include one or more magnetic materials, such as ferromagnetic, paramagnetic, super-paramagnetic, or any other material that responds to a magnetic field. The collection magnet can be configured to direct a magnetic field into the portion of subsurface vasculature 152. The magnetic field can cause the magnetically-reactive functionalized particles to collect in a lumen of that portion of the subsurface vasculature 152. The magnet may be an electromagnet that may be turned on during measurement periods and turned off when a measurement period is complete so as to allow the collected functionalized particles to disperse (e.g., circulate) through the vasculature.

iii. Signal Modulation

The wearable device may, in some cases, also include a modulation source. The signal-to-noise ratio (SNR) in the analyte detection systems described herein may be increased by causing the response signal transmitted from the subsurface vasculature 152 (or other body system) to be modulated with respect to the background. The modulation can thereby enable the sensors (or a signal processing system associated therewith) to distinguish between the response signal indicative of a physiological condition and background signals. In some cases, functionalized particles which are bound to an analyte of interest may generate a response signal which is modulated, while signals from unbound particles are not modulated (or modulated differently). Thus, such modulation can increase the system's sensitivity and ability to discern between target analytes present in the blood or other bodily fluids, and therefore binding to functionalized particles, versus other analytes, particles, cells, molecules, blood components, bone and tissues, etc. This can be particularly valuable with some methods of analyte characterization, such as optical methods, or where the target analytes are rare in the blood or are of a relatively small size and with fluorescence detection techniques, which can often suffer from low resolution because other tissues, cells, and molecules in the body may have some inherent fluorescent properties, creating a high level of background noise.

The modulation source may apply a modulation to the interrogating signal, which is configured to cause a corresponding modulation of the response signal. Specifically, the modulation source may be configured to modulate the response signal differently from a background signal. The background signal may include any signal transmitted from something other than what the system is monitoring, i.e., the target analyte(s). In some examples, the background signal may be generated by other molecules, cells, or particles in the blood or other bodily fluids; tissue, such as skin, veins, muscle, etc.; bone; or other objects present in the wearer's body. A background signal may be generated by excitation of these objects from the interrogating signal, such as by generating an autofluorescence signal, or due to some inherent property of these objects, such as, chemiluminescence, etc.

In some examples, the modulation source may be configured to modulate the response signal (transmitted from bound particles) differently than the unbound particle signal (transmitted from particles that are not bound or otherwise interacting with the target analyte(s)) such that the analyte response signal may be differentiated from the unbound particle signal. Such differentiation may be used to determine the number or percentage of particles bound to or interacting with the target analyte(s), which may be used to determine a concentration of the target analyte(s) in the blood or other bodily fluid, to determine if and to what extent the particles are being cleared from the body, etc.

The modulation source may be a physical construct or it may be a signal or energy applied to the body, or a combination thereof. In some cases, the modulation source may be configured to alter the spatial, optical magnetic, electric, acoustic, and/or physical properties of the bound particles. Accordingly, the modulation of the response signal may include spatial, temporal, spectral, thermal, magnetic, optical, mechanical, electrical, acoustic, chemical, or electrochemical type of modulation or any combination thereof.

F. Example In Vivo Physiological Measurements

Figure 4A:
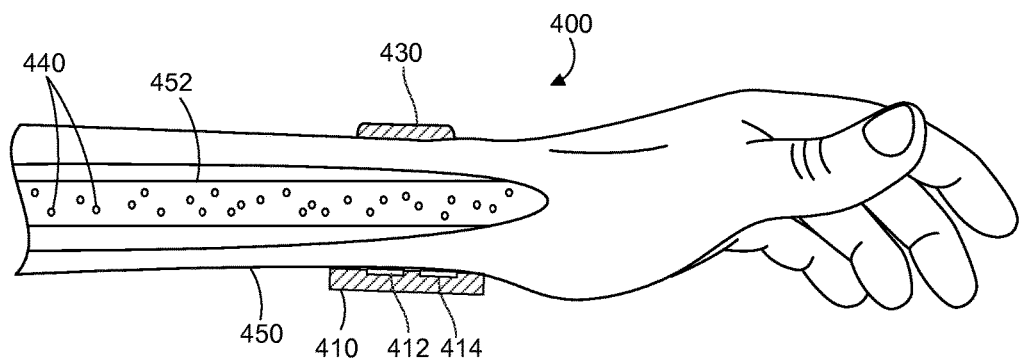
FIGS. 4A and 4B are side partial cross-sectional view of an example wrist-mounted device, while mounted on a human wrist.
Figure 4B:
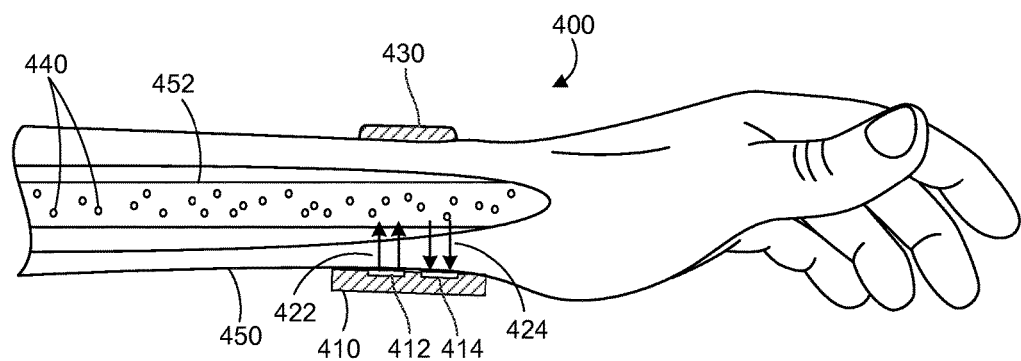

FIGS. 4A-4B and 5A-5B are partial cross-sectional side views of a human wrist illustrating example physiological measurement operations of various examples of wrist-mounted devices. In the example shown in FIGS. 4A and 4B, the wrist-mounted device 400 includes a measurement platform 410 mounted on a strap or wrist-band 430 and oriented on the anterior side 450 of the wearer's wrist. Measurement platform 410 is positioned over a portion of the wrist where subsurface vasculature 452 is easily observable. Functionalized particles 440 have been introduced into a lumen of the subsurface vasculature 452. In this example, measurement platform 410 includes a data collection system having both an emitter 412 and a detector 414. FIG. 4A illustrates the state of the subsurface vasculature 452 when measurement device 400 is inactive. The state of the subsurface vasculature during a measurement period is illustrated in FIG. 4B. At this time, signal source 412 is transmitting an interrogating signal 422 into the portion of subsurface vasculature and detector 414 is receiving a response signal 424 generated in response to the interrogating signal 422 (e.g., a fluorescent emission from the functionalized particles 540). The response signal 424 is related to the binding of a clinically relevant analyte present in the subsurface vasculature 452 to the functionalized particles 440. As described above, in some embodiments, an interrogating signal may not be necessary to generate a response signal related to the binding of an analyte to the functionalized particles 440.

Figure 5A:
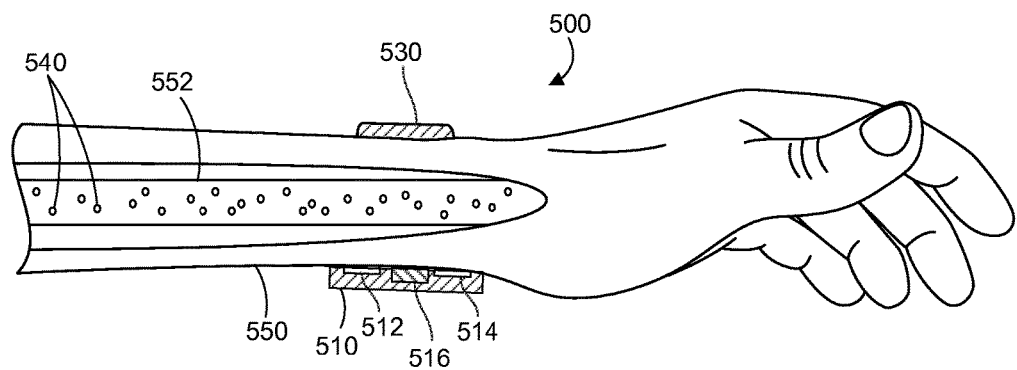
FIGS. 5A and 5B are side partial cross-sectional view of an example wrist-mounted device, while mounted on a human wrist.
Figure 5B:
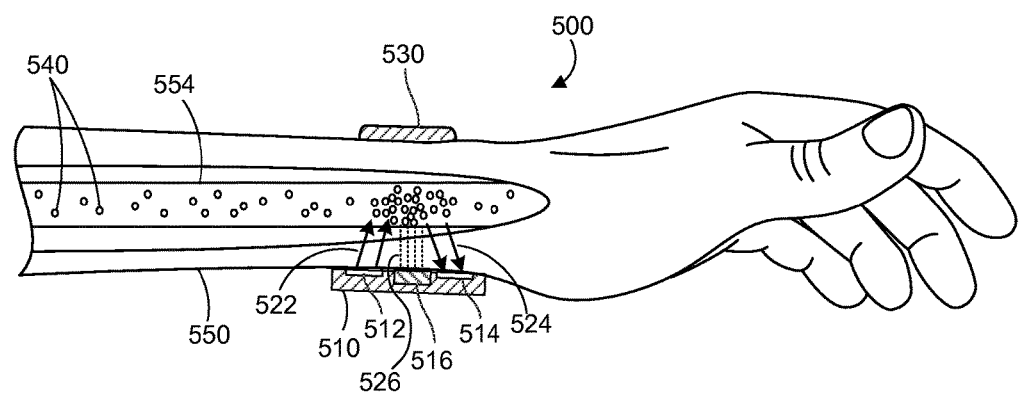

Similar to the system depicted in FIGS. 4A and 4B, FIGS. 5A and 5B illustrate a wrist-mounted device 500 including a measurement platform 510 mounted on a strap or wrist-band 530 and oriented on the anterior side 550 of the wearer's wrist. In this example, measurement platform 510 includes a data collection system having an emitter 512, a detector 514, and a collection magnet 516. Functionalized particles 540 have been introduced into the body of the wearer, and circulate through a lumen of the subsurface vasculature 552 of the wrist. The functionalized particles 540 may be a magnetic and/or paramagnetic such that the particles 540 may respond to an applied magnetic field (e.g., become attracted to a magnetic field 526 from the collection magnet 516). FIG. 5A illustrates the state of the subsurface vasculature 552 when measurement device 500 is inactive. The state of the subsurface vasculature 552 during a measurement period is shown in FIG. 5B. During a measurement, collection magnet 516 generates a magnetic field 526 sufficient to cause magnetic and/or paramagnetic functionalized particles 540 present in a lumen of the subsurface vasculature 552 to collect in a region proximal to the magnet 516. While the functionalized particles 540 accumulate in the proximal region due to the magnetic field 526, the emitter 512 may transmit an interrogating signal 522 into the portion of subsurface vasculature 552 and detector 514 can receive a response signal 524 generated in response to the interrogating signal 522 (e.g., a fluorescent emission from the functionalized particles 540). The response signal 524 is related to the binding of a clinically relevant analyte present in the subsurface vasculature 552 to the functionalized particles 540. As described above, in some embodiments, an interrogating signal may not be necessary to generate a response signal.

Additionally or alternatively, a collection magnet may be mounted in the wearable sensor device 500 on the mount 530, additionally or alternatively to the measurement platform 510. For example, a collection magnet may be situated along the posterior side of the wrist, opposite the anterior side 550. Such a collection magnet can be used similarly to the collection magnet 516 so as to accumulate the functionalized particles 540 in a region proximal to the measurement platform 510 during a measurement.

FIG. 5B illustrates the path of the interrogating signal 522 transmitted by the emitter 512 and the path of the response signal 524 detected by the detector 514 overlapping over a common portion of subsurface vasculature 552. In some examples, the emitter 512 and the detector 514 may be angled towards each other so that they are interrogating and detecting from essentially the same portion of subsurface vasculature. However, in some instances, such as in the example shown in FIG. 4B, the paths of the interrogating signal 422 transmitted by the emitter 412 and the response signal 424 detected by the detector 414 may not overlap.

III. Example Photocleavable Functionalized Particles

In some examples, the sensor devices described above obtain at least some of the health-related information by detecting response signals from functionalized particles. The response signal may provide an indication of a presence of the functionalized particles, or an indication of whether the functionalized particles have bound to a target analyte, or some other clinically-relevant information involving activity of the functionalized particles within the body. The particles can be functionalized by covalently attaching a functional group designed to selectively bind or otherwise recognize a particular clinically-relevant analyte. For example, particles may be functionalized with one or more aptamers to increase affinity to a target analyte or to detect multiple different targets. The target analyte may be a receptor associated with a particular type of cell, such as a cancerous cell. The functionalized particles may also include a variety of other chemical groups or compounds that are designed to perform particular operations, such as a fluorophore or other detectable label. The functionalized particle conjugates can be introduced into a living body by injection, ingestion, inhalation, transdermally, or in some other manner.

Figure 6A:
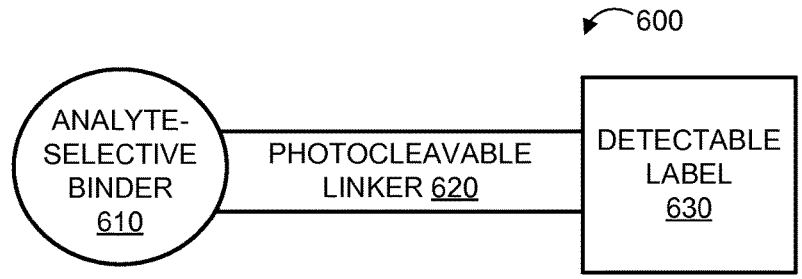
FIGS. 6A and 6B are functional block diagrams of a photocleavable functionalized particle.
Figure 6B:
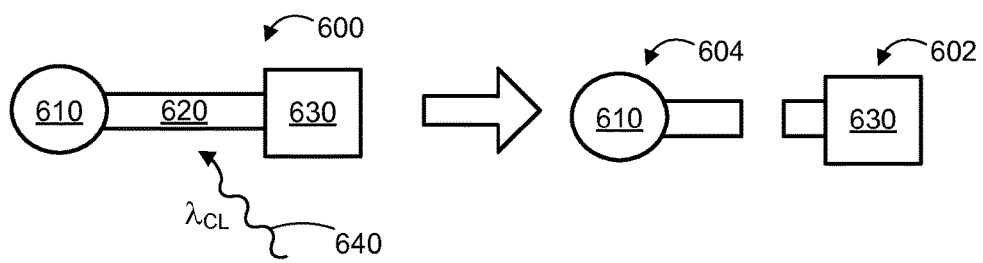

An example photocleavable functionalized particle 600 is represented by the diagram in FIG. 6A. The functionalized particle 600 includes an analyte-selective binder 610 that is coupled to a detectable label 630 via a photocleavable linker 620. The photocleavable linker 620 can be a functional group that includes one or more chemical bonds that are modified in response to absorbing light at a particular wavelength. The photo-initiated cleaving reaction cleaves the photocleavable linker 620 and results in the analyte-selective binder 610 becoming separated from the detectable label 630. FIG. 6B is a diagram that illustrates the photo-initiated cleaving reaction. A light source can emit light 640 that includes light at a cleaving wavelength $\lambda$CL toward the particle 600. Upon absorbing a photon at the cleaving wavelength $\lambda$CL, one or more chemical bonds within the photocleavable linker 620 are broken and/or rearranged such that the photocleavable linker 620 no longer couples the analyte-selective binder 610 to the detectable label 630. As a result, following the photocleaving, the particle 600 is divided into a first functionalized particle 604, which includes the analyte-selective binder 610, and a second functionalized particle 602, which includes the detectable label 630.

Before being cleaved, the photocleavable linker 620 may couple the detectable label 630 and the analyte-selective binder 610 in a variety of different configurations in which a particle is used as a matrix or scaffold for immobilizing different functional groups. For instance, the analyte-selective binder 610 may be coupled to a particle, and the particle may also be coupled to a first side of the photocleavable linker 620, and a second side of the photocleavable linker 620 can be coupled to the detectable label 630. In another example, the detectable label 630 may be coupled to a particle, and the particle may also be coupled to the first side of the photocleavable linker 620, and the second side of the photocleavable linker 620 can be coupled to the analyte-selective binder 610. The analyte-selective binder 610 may be an aptamer, an antibody, or another chemical functional group that is configured to bind to one or more target analytes with a particular affinity and/or selectivity. The detectable label 630 may be a fluorophore, a molecular dye, or another contrast agent that may be detected within a living body in vivo using an external sensor device.

In another example, a photocleavable linker may couple a detectable label to a molecular payload, such as a drug or another biologically interactive agent. The molecular payload may be initially biologically inactive, and become biologically active in vivo in response to an externally applied stimulus, such as cleaving of the photocleavable linker, or upon absorbing directed energy.

A. Example Particles

The particles could be, for example, microparticles or nanoparticles. The particles may be made of biodegradable or non-biodegradable materials. For example, the particles may be made of polystyrene. Non-biodegradable particles may be provided with a removal means to prevent harmful buildup in the body. Generally, the particles may be designed to have a long half-life so that they remain in the vasculature or body fluids over several measurement periods. Depending on the lifetime of the particles, however, the user of the wearable device may periodically introduce new doses of particles into the vasculature or body fluids.

The term "particle" is used in its broadest sense and the particles described herein may take the form of any fabricated material, a molecule, tryptophan, a virus, a phage, etc. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Nanoparticles have been the subject of considerable research interest, particularly in the fields of diagnostics and drug therapy. Nanoparticles are defined as particulate dispersions or solid particles with a size ranging from 10 to 1000 nm. Nanoparticles can be synthesized by a variety of methods including the sol-gel process, dispersion of preformed polymers, polymerization of monomers, ionic gelation or coacervation of hydrophilic polymers. Nanoparticles can be prepared from a variety of materials include metals, proteins, polysaccharides, or synthetic polymers. The selection of materials can be dependent on many factors including (a) the size of the nanoparticles required; (b) desired surface characteristics such as charge and permeability; (c) degree of biodegradability, biocompatibility and toxicity; and (d) if the nanoparticle is used as a carrier to deliver a payload such as a drug, the inherent properties of the drug such as the aqueous solubility and stability. Particle size and size distribution can be important characteristics of nanoparticle systems as they determine the in vivo distribution, biological fate, toxicity, and the targeting ability of the nanoparticle systems. In addition, they can also influence the drug loading, drug release and stability of nanoparticles. Surface modification of nanoparticles can drastically improve biocompatibility, half-life and biodistribution.

Further, the particles may be formed from a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect the particles in an area of subsurface vasculature during a measurement period, such as described in connection with FIGS. 5A-5B. Such collection may not only increase the differential velocity between particles and analytes, hence surveying a much larger volume per unit time, but may also enhance the signal for subsequent detection.

Suitable particles including nanoparticles can be prepared by any suitable means. See, for instance, Y. Deng et al., *J. Magnetism and Magnetic Materials*, Vol. 257, pp. 69-78 (February 2003) and W. Fang et al., *J. Mater. Chem*, 2010, Vol. 20, pp. 8624-8630 DOI:10.1039/C0JM02081H, both describing preparation of polymeric magnetic particles, which references are incorporated by reference in their entirety. Suitable particles including magnetic microparticles and nanoparticles are also available commercially. See, for instance, Chemicell GmBH, Berlin, Germany; and Ademtech Inc., New York, N.Y., USA.

Nanoparticles may act as scaffolds for immobilization (e.g., binding) of various functional groups. In some cases, the nanoparticles can include a number of binding sites for coupling with functional groups to create particle conjugates that are configured to carry out particular functions. Among other possibilities, such functional groups may result in a particle conjugate that has a desired avidity and/or specificity to one or more particular target analytes, or that facilitate detection via fluorescence (or a change in fluorescence), or that release a molecular payload, such as a drug, ion, or a molecular sensor. Further, the functional groups may perform those operations in response to predetermined stimuli encountered in vivo, such as binding to (or releasing from) a target analyte, absorbing a predetermined level of directed energy, encountering an environment with a particular pH. Thus, operations performed by the functionalized particles within a living body may be partially influenced by stimuli provided from an exterior of the body. In some cases, a stimulus may be applied at a first region of a body so as to interact with functionalized particles in the first region of the body. Measurements can then be obtained from a second region of the body related to presence and/or activity of functionalized particles in the second region. Because the circulatory system of the body allows the functionalized particles in different regions of the body to circulate, the measurements from the second region of the body can be used to determine physiological characteristics of the first region. Two examples of in vivo detection of indications of stimulus-altered functionalized particles are provided herein in connection with FIGS. 7A-7D, 8A-8C, 9A-9D, and 10A-10C.

Any suitable method for conjugating a functional group to a particle may be used. See, for instance, well-known click chemistry which entails labeling with an azide or alkyne group and coupling the labeled functional group to an alkyne/azide group on the particle. Alternatively, the functional group may be labeled with an NH2 group and then coupled to —COOH group on the particle using 1-ethyl-3-[3-dimethylaminopropyl]carbodiimide hydrochloride (EDC or EDAC) cross-linking agent (commercially available from Thermo Fisher Scientific, Inc., Rockford, Ill., USA).

B. Analyte-Selective Binder

Sometimes referred to as "synthetic antibodies," aptamers are pre-selected single-stranded oligonucleotide (e.g., DNA or RNA) or peptide molecules that bind to specific target molecules including proteins and peptides with affinities and specificities that are comparable to antibodies. These molecules can assume a variety of shapes due to their propensity to form helices and single-stranded loops with specific binding pockets, explaining their versatility in binding to diverse targets. Their specificity and characteristics are not directly determined by their primary sequence but by their tertiary structure which is analogous to the globular shape of tRNA. Aptamers have a wide range of applications including diagnostics and therapeutics and can be chemically synthesized using known techniques. Furthermore, aptamers can offer a number of advantages over traditional antibodies including avoiding the need to specifically know the precise epitopes or biomarkers themselves. Finally, aptamers are typically non-immunogenic, easy to synthesize, characterize, modify and exhibit high specificity and affinity for their target antigen.

The conjugation of an analyte-selective functional group, such as an aptamer, to a nanoparticle allows for the detection and quantization of target analytes in vivo. For example, an aptamer conjugate can act as a binding agent, a molecular switch or both, to measure the in vivo levels of target analytes such as biomolecules, ions, and/or particular cells (e.g., via receptors associated with those cells).

The target analyte could be any analyte that, when present in or absent from the blood, or present at a particular concentration or range of concentrations, may be indicative of a medical condition or indicative that a medical condition may be imminent. For example, the clinically-relevant analyte could be an enzyme, hormone, protein, or other molecule. In one relevant example, certain protein biomarkers are known to be predictive of an impending arterial plaque rupture. Such protein biomarkers are known to be present in the blood only directly leading up to and at the onset of an arterial plaque rupture. Plaques that rupture cause the formation of blood clots that can block blood flow or break off and travel to another part of the body. In either of these cases, if a clot blocks a blood vessel that feeds the heart, it causes a heart attack. If it blocks a blood vessel that feeds the brain, it causes a stroke. If blood supply to the arms or legs is reduced or blocked, it can cause difficulty walking and eventually gangrene. The presence of these protein biomarkers in the vasculature may be detected, and the medical condition (i.e., stroke, heart attack) prevented, by providing particles functionalized with an aptamer that will selectively bind to this target analyte. Representative examples of target analytes include, without limitation, serum glucose, calcium, blood urea nitrogen, creatinine, creatine kinase, sodium, potassium chloride, carbon dioxide, oxygen, serum calcium, serum total protein (TP), human serum albumin, bilirubin, alkaline phosphatase (ALP) aspartate amino transferase (AST), alanine amino transferase (ALT), glucose and insulin. Additional representative target analytes include lactate, cardiac enzymes, pharmaceuticals, hormones, cytokines, growth factors, circulating nucleic acids, circulating peptides, circulating viruses, and circulating cells.

The binding (or release) of a particle conjugate to (from) a target analyte in vivo may trigger a conformational change that permits subsequent binding of a detectable label such as a fluorophore, increase or decrease fluorescence via FRET, release/bind a secondary detectable molecule, or cause targeted release of a molecular payload such as a drug, ion, or a sensor. For aptamer-particle conjugates targeted to a receptor on a cell surface, a conformational change may occur which can increase or decrease fluorescence via FRET, lead to endocytosis followed by a pH change that leads to a detectable conformational change of the aptamer or lead to endocytosis followed by a pH change in the endosome which may be detected by a pH sensitive dye. Two or more different aptamers may be used to improve avidity to a target analyte or to create particles that can detect multiple different target analytes. Binding of the particle to a target analyte (e.g., via conjugated functional group) may be detected with or without a stimulating signal input. The term "binding" is understood in its broadest sense to include any detectable interaction between the particle and the target analyte.

Analyte-selective binders, such as aptamers, can be used in diagnostic procedures, or even in therapy to destroy a specific target, such as antitumor therapy or targeted chemotherapy. The particles can be designed to remove from the body or destroy the target analyte once bound to the aptamer. Additional functional groups can be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus. The particles could also be used for in vivo enrichment and extraction of low abundance circulating biomarkers. For instance, aptamer-particle conjugates can be circulated and any biomolecules bound to the aptamers may be eluted off and analyzed in vitro.

Aptamer-particle conjugates can be prepared by any suitable means. For instance, aptamers have been developed that are specific for target analytes including cell types. See, for instance, K. Sefah et al. *Nature Protocols*, Vol. 5, pp. 1169-1185 (June 2010) describing aptamers specific for any cell type and Q. Shen et al., *Adv. Mater.*, Vol. 25, pp. 2368-2373. DOI: 10.1002/adma.201300082, describing preparation of aptamers specific for A549 non-small cell lung cancer cells, which are incorporated by reference in their entirety. Aptamers are also available commercially. See, for instance, OTCbiotechnologies, LLC, San Antonio, Tex., USA and Base Pair Biotechnologies, Inc., Houston, Tex., USA; and AMS biotechnology (Europe) LTD, Abingdon, UK.

C. Photocleavable Linker

As noted above, a photocleavable linker or spacer can be used to conjugate a functional group to a particle. In particular, as shown in FIG. 6B, the photocleavable linker 620 can be used to couple an analyte-selective binder 610 to a detectable label 630. Upon absorbing light at a cleaving wavelength λCL, the photocleavable linker 620 undergoes a reaction which causes the analyte-selective binder 610 to become separated from the detectable label 630. Photocleavable linkers are commercially available. See for instance Integrated DNA Technologies, Inc., Coralville, Iowa, USA; and Ambergen, Inc., Watertown, Mass., USA).

D. Detectable Label

Figure 6C:
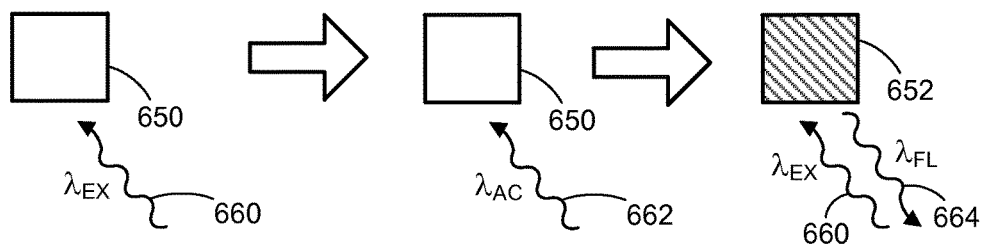
FIGS. 6C and 6D are functional block diagrams of detectable labels that exhibit a modified response signal in response to a stimulus.
Figure 6D:
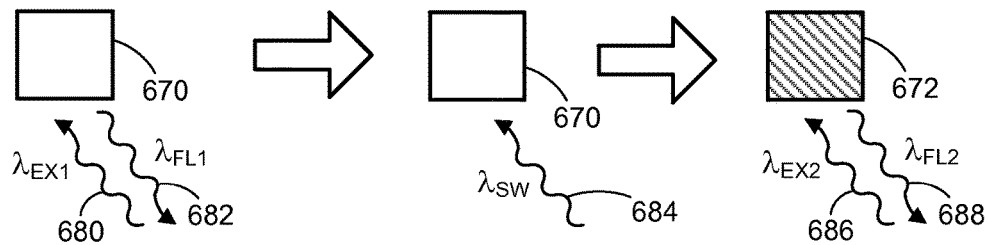

The detectable label 630 may be any compound or molecule which can be detected in vivo using an external sensor device. For example, the detectable label 630 may be a fluorophore, such as a fluorescent protein or small molecule or an autofluorescent, luminescent or chemiluminescent marker, which generates a responsive signal. In some examples, the detectable label 630 may be configured to generate different response signals depending on whether the photocleavable linker 620 has been cleaved or not. For example, the detectable label 630 may generate a first response signal while part of the functionalized particle 600, and a different response signal while part of the particle 604 that is separated from the analyte-selective binder 610. In some examples, the detectable label 630 may be configured to temporarily or irreversibly generate a different responsive signal upon receiving external stimulus, such as an electromagnetic, acoustic, optical, or mechanical energy. Fluorophores which modify their behavior in response to absorbing directed energy may be desirable in some applications, because the modification may allow for a detection system to determine whether the fluorophore has experienced particular stimuli while in vivo. There are several classes of fluorophores which exhibit different behaviors upon absorbing light at particular wavelengths. FIGS. 6C and 6D are diagrams that illustrate a photoactivated fluorophore and a photoswitchable fluorophore, respectively.

i. Photoactivated Fluorophore

FIG. 6C is a diagram that shows a photoactivated fluorophore initially in an inactive state (650), and then in an active state (652) after absorbing activating light 662 at an activating wavelength λAC. In the active state (652), which is represented by diagonal fill pattern for purposes of distinguishing from the inactive state (650), the fluorophore emits fluorescent light 664 at a fluorescence wavelength λFL in response to absorbing excitation light 660 at an excitation wavelength λEX. However, in the inactive state (650), the fluorophore fluoresces with less energy than in the active state (652), or does not fluoresce at all, when exposed to the excitation light 660 at the excitation wavelength λEX. The absorption of activating light 662 may induce a reaction that alters a chromophore/fluorophore configuration of the photoactivated fluorophore. One example of a photoactivated fluorophore is photoactivated green fluorescent protein, PA-GFP, which is "switched on" from a low fluorescent state to a high fluorescent state upon activation by a short light pulse in the blue or violet spectrum.

The photoactivated fluorophore may be selected such that the activation wavelength λAC differs from the excitation wavelength λEX to mitigate inadvertent activation while interrogating the fluorophore. In some cases, the photoactivated fluorophore may be selected such that λAC, λEX, and λFL are all near a range of about 700-900 nanometers, which provides a desirable penetration depth into tissue during in vivo applications. In some examples, the activation wavelength λAC and cleaving wavelength λCL may be approximately the same wavelength or wavelengths that are relatively close together. As such, a single light source may emit light with a spectrum that includes both λAC and λCL and thereby simultaneously cleave a fluorophore from a functionalized particle and also transition the fluorophore from a low fluorescence state to a high fluorescence state. In other examples, λAC and λCL may be far enough apart that cleaving and photoactivation can be performed separately (e.g., by two different light sources). For instance, depending on the photoactivated fluorophore and photocleavable linker selected, photoactivating may require application of light at wavelength λAC for a first length of time and first intensity, whereas photocleaving may require application of light at wavelength λCL for a second length of time and second intensity. If the two effects are initiated by light at two different wavelengths, then light with the specified parameters can be applied for both photocleaving and photoactivation without interfering with initiation of the other. Moreover, light from two different light sources (or a single light source) with different wavelengths and/or intensities may be applied to a single region of the body simultaneously.

ii. Photoswitchable Fluorophore

FIG. 6D is a diagram that shows a photoswitchable fluorophore initially in a first fluorescence state (670), and then in a second fluorescence state (672) after absorbing switching light 684 at a switching wavelength λSW. In the first state (670), the fluorophore emits fluorescent light 682 at a first fluorescence wavelength λFL1 in response to absorbing excitation light 680 at a first excitation wavelength λEX1. In the second state (672), which is represented by diagonal fill pattern for purposes of distinguishing from the first state (670), the fluorophore emits fluorescent light 688 at a second fluorescence wavelength λFL2 in response to absorbing excitation light 686 at a second excitation wavelength λEX2. The first and second fluorescence wavelengths λFL1, λFL2 differ from one another, and the first and second excitation wavelengths λEX1, λEX1 differ from one another. The absorption of switching light 684 may induce a reaction that alters a chromophore/fluorophore configuration of the photoswitchable fluorophore.

Some examples of photoswitchable fluorophores may return to the first state (670) upon absorbing a second stimulus (e.g., light at another wavelength). The photoswitchable fluorophore may also return to the first state (670) after some length of time (e.g., the fluorophore may operate in the second state (672) while in an energized state, and eventually relax back to the first state (670)).

Another example of a photo-modified fluorophore is a photoconvertible fluorophore, which may be similar to the photoswitchable fluorophores, but photo-initiated modifications in the fluorescent spectrum are generally irreversible. One example of a photoconvertible fluorophore is a fluorescent protein referred to as Kaede, which irreversibly switches emission from green to red after absorbing UV light. Other examples are also possible, and can be selected to suit a particular implementation. One example of a photoswitchable fluorophore is a fluorescent protein referred to as Kindling fluorescent protein. Other examples are also possible, and can be selected to suit a particular implementation.

The photoswitchable and/or photoconvertible fluorophores may be selected such that the switching wavelength λSW differs from the excitation wavelengths λEX1, λEX2 to mitigate inadvertent switching while interrogating the fluorophore. In some cases, the photoswitchable and/or photoconvertible fluorophore may be selected such that λSW, λEX1, λEX2, λFL1, and λFL2 are all near a range of about 700-900 nanometers, which provides a desirable penetration depth into tissue during in vivo applications. In some examples, the switching wavelength λSW and cleaving wavelength λCL may be approximately the same wavelength or wavelengths that are relatively close together. As such, a single light source may emit light with a spectrum that includes both λSW and λCL and thereby simultaneously cleave a fluorophore from a functionalized particle and also switch the fluorophore from a first fluorescence state to a second fluorescence state. In other examples, λSW and λCL may be far enough apart that switching and photoactivation can be performed separately (e.g., by two different light sources). For instance, depending on the photoswitchable fluorophore and photocleavable linker selected, photoswitching may require application of light at wavelength λSW for a first length of time and first intensity, whereas photocleaving may require application of light at wavelength λCL for a second length of time and second intensity. If the two effects are initiated by light at two different wavelengths, then light with the specified parameters can be applied for both photoswitching and photocleaving without interfering with initiation of the other. Moreover, light from two different light sources (or a single light source) with different wavelengths and/or intensities may be applied to a single region of the body simultaneously.

IV. Example Detection Systems

An in vivo detection system may include a sensor device that is configured to obtain a response signal indicative of a presence of functionalized particles within a living body. The detection system can also include an energy source that is configured to transmit directed energy into the body so as to interact with the functionalized particles while they are in the body. The functionalized particles may include two portions that are coupled by a cleavable linker configured to undergo a reaction that separates the two portions in response to absorbing directed energy from the energy source, and at least one of the separated portions can be detectable using the sensor device. For example, the linker may be a photocleavable linker which has one or more chemical bonds that are modified in response to absorbing light at a particular wavelength (e.g., cleaving light). In response to the photocleavable linker absorbing light, the two portions of the original functional particle can become separated. Following application of directed energy (e.g., cleaving light) to separate functionalized particles within the body, measurements indicative of the detectable portion of the particles may be obtained using the sensor device, and those measurements can be used to determine an amount of the functionalized particles that were separated by the directed energy. The in vivo detection systems described herein thus provide a system and operation that allows for physiological information about one area of a living body to be inferred from measurements obtained from another area of the body.

A. Example Analyte Detection System

Figure 7A:
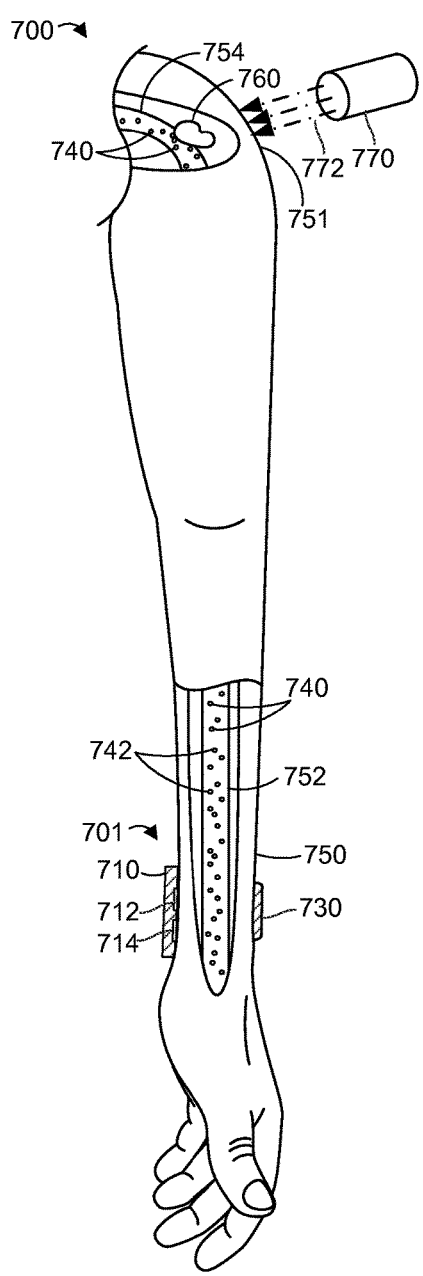
FIG. 7A is a partial cross-sectional view of an analyte detection system used to obtain measurements of physiological parameters.
Figure 7B:
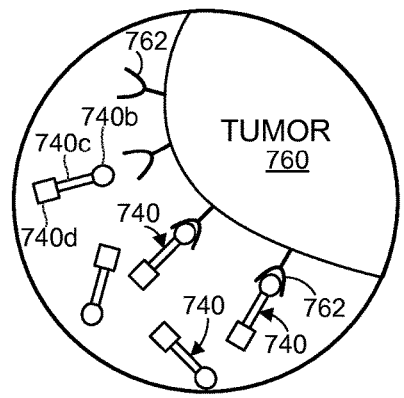
FIGS. 7B, 7C, and 7D are diagrams illustrating interaction of functionalized particles with a target analyte and with absorbed light during an analyte detection process.
Figure 7C:
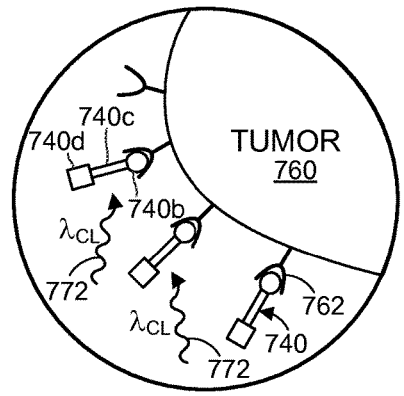
Figure 7D:
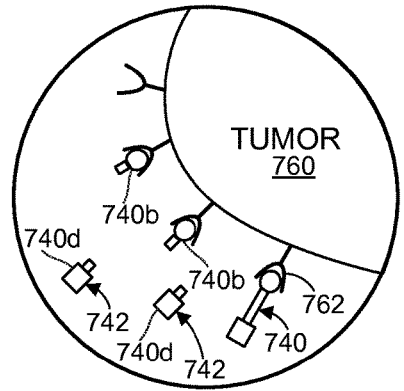

An analyte detection system is described in connection with FIGS. 7A-7D and 8A-8C. FIG. 7A is a partial cross-sectional view of an analyte detection system 700. FIGS. 7B, 7C, and 7D are diagrams illustrating interaction of functionalized particles with a target analyte and with absorbed light during an analyte detection process. Functionalized particles 740 are introduced into a living body (e.g., via injection, ingestion, or inhalation). The functionalized particles 740 disperse throughout the body via the circulatory system. As shown in FIG. 7A, which is a view of an arm including partial cross-sections at the shoulder 751 and forearm 750, the functionalized particles 740 are distributed throughout the subsurface vasculature 754 near the shoulder 751 and the subsurface vasculature 752 of the forearm 750. The circulatory system of the body may circulate the functionalized particles 740 through a network of lumens in the subsurface vasculature such that some functionalized particles from different parts of the living body eventually pass in proximity to a wearable sensor device 701 where the particles 740 can be interrogated. The analyte detection system 700 includes a wearable sensor device 701 mounted to a wrist, and a light source 770 arranged to emit light 772 toward the shoulder 751. A tumor 760 may be present within the shoulder 751, and some of the circulating functionalized particles 740 may become proximate to the tumor 760 via the subsurface vasculature 754 in the shoulder 751.

i. Photocleavable Functionalized Particles for Analyte Detection

The functionalized particles 740, which are shown in FIGS. 7B-7D, each include a detectable label 740*d* and an analyte-selective binder 740*b* that are coupled via a photocleavable linker 740*c*. The functionalized particles may be similar to the particles 600 described in connection with FIGS. 6A-6B. The analyte-selective binder 740*b* may be configured to bind to a receptor 762 associated with a tumor 760. For instance, the receptor 762 may be a biomarker associated with a cancerous cell, such as a binding site present on the cell surface. The analyte-selective binder 740b can then be designed to bind to the receptor 762 with a desired affinity and/or selectivity and then coupled to a nanoparticle.

The detectable label 740d may include any of the detectable labels described above in connection with FIGS. 6A-6D, including the various fluorophores that are modified in response to absorbing directed energy. As such, a stimulus may be applied to a particular region of the body (e.g., via the light source 770 at the shoulder 751), and a subsequent detection of fluorophores modified in accordance with the stimulus (e.g., via the sensor device 701 at the wrist 750) may be determined to be from fluorophores that came from the particular region of the body.

ii. Analyte-Detection System Working Principle

The light source 770 can be a light source that emits light 772 at a wavelength that includes a cleaving wavelength λCL for separating two portions of the functionalized particles 740. In particular, the light 772 can cause a detectable portion 742 of the functionalized particle 740 to separate from an analyte-selective binding portion of the functionalized particle, and the detectable portion 742 can then be distributed through the circulatory system separately from the analyte-selective portion of the functionalized particle 740.

The wearable sensor device 701 may be implemented as any of the sensor devices 100, 200, 300, 400, 500 described above, and can include a variety of sensors for detecting response signals indicative of a presence of functionalized particles within the subsurface vasculature 752 of the body. As shown in FIG. 7A, the sensor device 701 may include a sensor housing 710 with an emitter 712 and a detector 714. The sensor device 701 is mounted via a strap 730 such that the sensor housing 710 is situated over the anterior side of the wearer's wrist. During measurement, the emitter 712 can direct energy (e.g., an excitation light) into the subsurface vasculature 752 of the wrist, and the detector 714 can detect a response signal from the functionalized particles 740 (and detectable portions 742 of separated functionalized particles) within the subsurface vasculature 752. The detector 714 may be, for example, a photosensor (e.g., a light-sensitive element that generates an output signal related to energy of light incident on the light-sensitive element) that detects a fluorescent emission generated by the functionalized particles in response to the interrogating signal from the emitter 712. The sensor device 701 may further be configured to distinguish between functionalized particles 740 which have not been photocleaved (e.g., from detectable labels 740d included in a functionalized particle 740), and detectable portions 742, which have been photocleaved from the analyte-selective portion (e.g., from detectable labels 740d included in a detectable portion 742).

The functionalized particles 740 circulate through the body. Upon encountering the tumor 760, some of the functionalized particles 740 bind to the tumor 760 via the affinity of the analyte-selective binder 740b to the receptor 762 on the cells of the tumor 760. This binding of the functionalized particles 740 localizes them proximate to the tumor 760. Over time, a relatively large concentration of the dispersed functionalized particles 740 may accumulate near the tumor 760. Subsequently, the light source 770 is used to emit cleaving light 772 toward the shoulder area 751, as shown in FIG. 7C. The cleaving light 772 cleaves at least some of the photocleavable linkers 740c that were bound to the tumor 760. As shown in FIG. 7D, the cleaving light 772 separates the functionalized particles 740 into a portion that can remain bound to the tumor 760 (via the analyte-selective binder 740b) and a detectable portion 742 that includes the detectable label 740d.

Upon applying the cleaving light 772, a number of detectable portions 742 that had been localized at the tumor 760 migrate into the circulatory system of the body, where they may be eventually detected by the sensor device 701. For example, as a result of the application of the cleaving light 772, detectable portions 742 may be released from the tumor 750, enter the lumen of vasculature 754 in the shoulder 751, and then travel through the circulatory system to vasculature 752 in the wrist. Thus, the application of the cleaving light 772 via the light source 770 at a given location of the body may be used as a probe to test for the presence of the tumor 760 (or another target analyte). If the sensor device 701 detects an increase in the response signal due to the detectable portions 742 during some measurement interval that follows application of the cleaving light 772, it may be concluded that a relatively large number of the functionalized particles were localized in the region where the cleaving light was applied. By extension then, it may further be concluded that the region where the cleaving light was applied includes the target analyte (e.g., the receptors 762 associated with the tumor 760).

iii. Example Operation of the Analyte Detection System

Figure 8A:
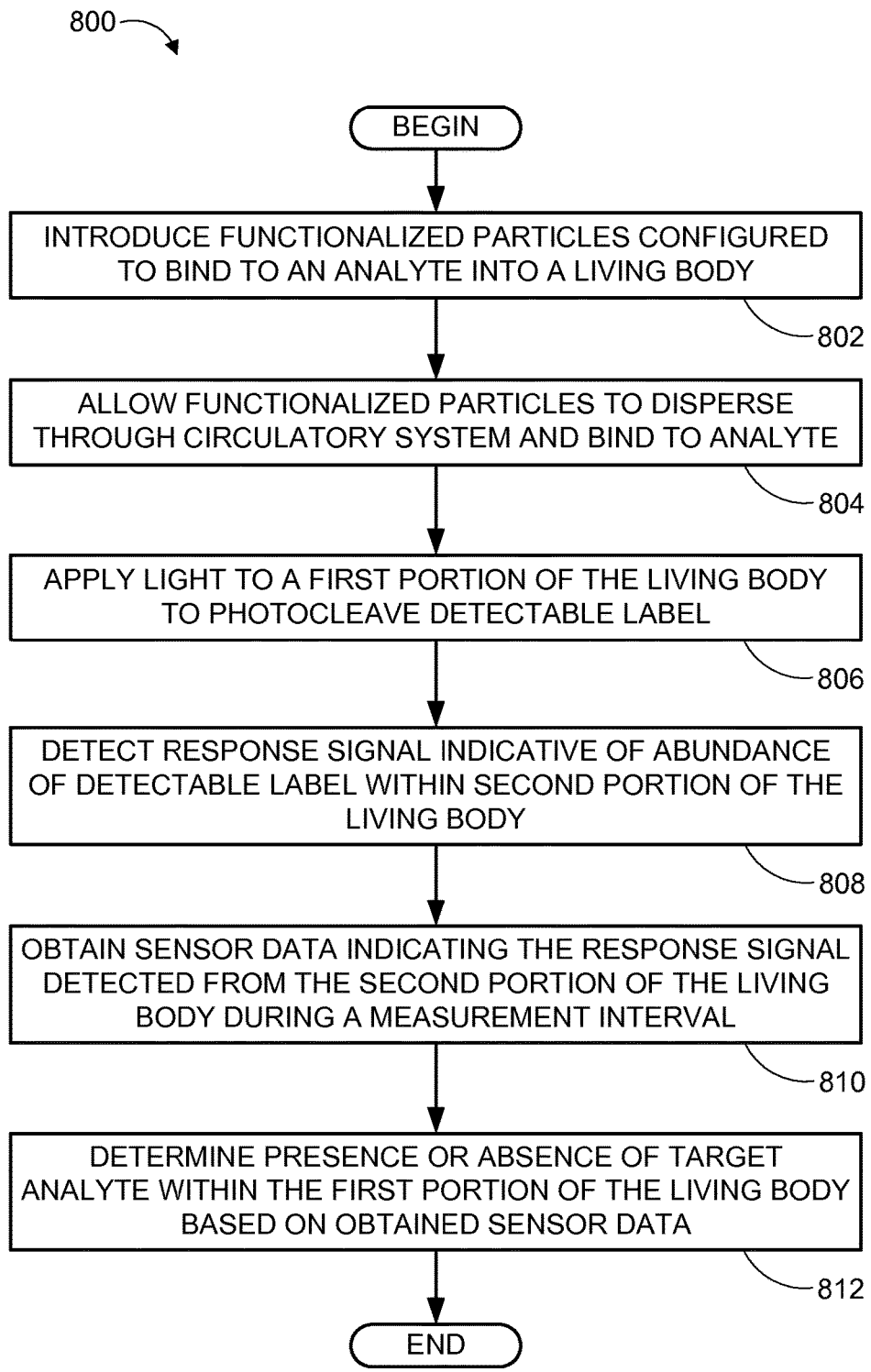
FIG. 8A is a flowchart of an example process for operating an analyte detection system.
Figure 8B:
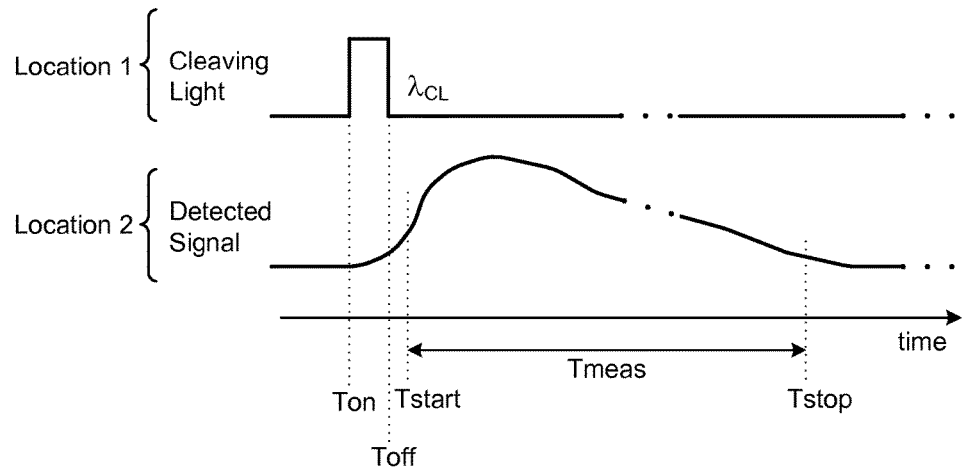
FIGS. 8B and 8C are timing diagrams illustrating operation of the light source(s) and detected response signals during an analyte detection process.
Figure 8C:
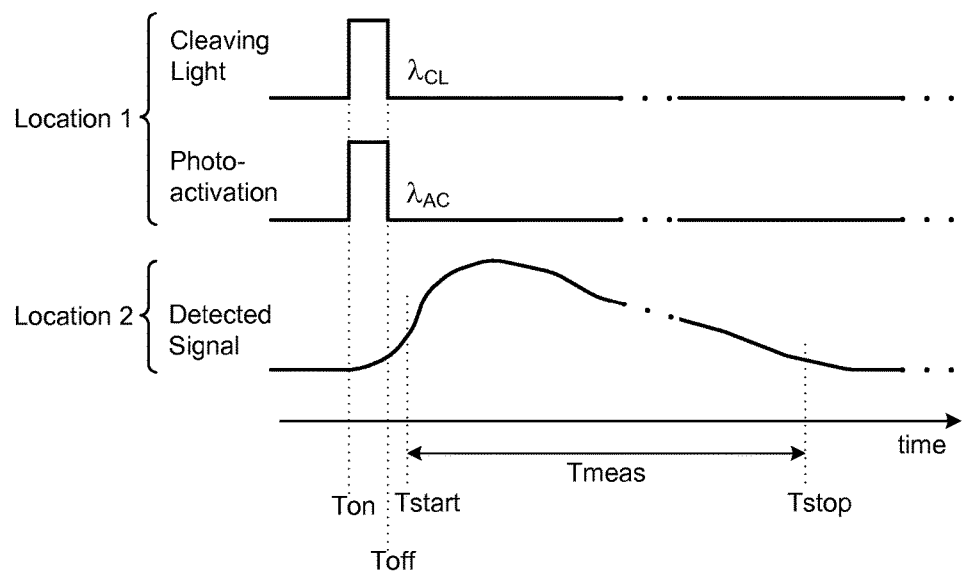

FIG. 8A is a flowchart of an example process 800 for operating an analyte detection system, such as the analyte detection system 700. FIGS. 8B and 8C are timing diagrams illustrating operation of the light source(s) and detected response signals during an analyte measurement process. The following description of the process 800 references the timing diagrams of FIGS. 8B-8C and also the example system 700 shown in FIGS. 7A-7D.

At block 802, functionalized particles that are configured to bind to a target analyte are introduced into a living body. As noted above, the functionalized particles may be introduced by injection, inhalation, ingestion, etc. The functionalized particles can include any number of analyte-selective binders designed to bind to one or more target analytes with a desired affinity and/or specificity. In addition, the analyte-selective binder is coupled to a detectable label through a photocleavable binder. For example, the functionalized particles 740 include the detectable label 740d coupled to the analyte-selective binder 740b through the photocleavable binder 740c.

At block 804, the functionalized particles introduced in block 802 are allowed to disperse through the circulatory system of the body and bind to the target analyte. As noted above, the speed at which the functionalized particles are dispersed through the circulatory system may depend in part on a number of factors of the particles themselves, including the size, materials, etc., as well as factors related to the in vivo environment of the living body (e.g., blood pressure, density of target analytes encountered, etc.). Thus, the duration of the time for which the functionalized particles are allowed to disperse may be based in part on a number of measured parameters, predictions, and/or empirical results.

At block 806, light is applied to a first portion of the living body to photocleave the detectable label from the portion of the particle configured to bind to the target analyte. For example, as shown in FIGS. 7B-7D, application of the cleaving light 772 causes the functionalized particle 740 to separate into the detectable portion 742 and a portion that remains bound to the tumor 760. The photocleaving light can be applied at a particular wavelength and for a particular duration, which each may depend on the particular photocleavable linker being used. In addition, the applied photocleaving light may be selected in accordance with one or more safety parameters so as to, for example, limit an energy dosage of radiation applied to a given area and/or volume of the living body. The application of the photocleaving light at wavelength λCL to the first location of the body is shown in FIG. 8B, in which the photocleaving light is applied for a duration that spans from an initial time Ton to an end time Toff. Of course, depending on a particular implementation, the photocleaving light may be applied in other manners as well, such as an example in which the power of the cleaving light during application is non-continuous.

In addition, as shown in FIG. 8C, an activation light, or another stimulus to modify a detectable response signal of the detectable label 740$d$, may be also be applied to the first location of the body at or near the time of application of the photocleaving light. As described in connection with FIG. 6C, the activation light at an activation wavelength λAC can cause the response signal from the detectable label to be modified, and therefore distinguishable from detectable labels that have not been exposed to the activation light. In another example, the detectable label 740$d$ may be a photoswitchable fluorophore as described in connection with FIG. 6D, in which case a switching light at a switching wavelength λSW may be applied at or near the same time as the cleaving light. In some cases, the light source 770 may emit light 772 that includes light at both the activation wavelength λAC (or switching wavelength λSW) and the cleaving wavelength λCL, such that the functionalized particles may be cleaved and their response signal modified simultaneously. In some cases, photoactivation of the detectable label 740$d$ may be induced by light at an activation wavelength λAC that is near to (or the same as) the cleaving wavelength λCL (or switching wavelength λSW).

At block 808, a response signal is detected that is indicative of an abundance of the detectable label within a second portion of the body. For example, the wearable sensor device 701 may be used to detect the presence of the detectable label 740$d$ on the functionalized particles and/or the detectable portions 742 of cleaved particles within the vasculature 752 of the forearm 750. The sensor device 701 may emit an excitation signal into the subsurface vasculature 752 via the emitter 712, and then detect a fluorescent response signal using the detector 714.

In an example in which the detectable labels 740$d$ in the first portion of the living body were modified via activation light, as in FIG. 8C, the sensor device 701 may be configured to distinguish between response signals from the cleaved detectable portion 742 and the uncleaved functionalized particles 740. In some cases, the sensor device 701 may detect response signals preferentially from the cleaved detectable portions 742. For instance, if the detectable labels are photoswitchable fluorophore or a photoactivated fluorophore, and switching or activating light was applied to the first location of the body near the time of the cleaving light, then the sensor device 701 may emit an interrogating light and/or detect a responsive fluorescent light that corresponds only to the modified version of the fluorophore.

At block 810, sensor data that indicates the response signal detected from the second portion of the body during a measurement interval is obtained using the sensor device. As shown in FIGS. 8B-8C, the measurement interval can be a period of time that begins at a start time Tstart, lasts for period Tmeas, and ends at a stop time Tstop. The start time may have a relationship with the time(s) at which the cleaving light is applied (i.e., Ton and/or Toff). For example, the start time Tstart may begin at a time at which detectable portions 742 of cleaved functionalized particles are expected to disperse from the shoulder 751, where they were localized at the tumor 760, to the wrist 750, where their presence can be detected via the sensor device 701. Thus, Tstart may be selected based in part on measured, predicted, and/or empirically derived factors, such as blood pressure, pulse rate, distance between the first and second locations of the living body, through the circulatory system, among other factors. Similarly, the duration Tmeas of the measurement interval can also be selected based on a variety of factors related to an expected period in which detectable portions 742 of cleaved functionalized particles are expected to disperse from the shoulder 751 to the wrist 750. In some cases, the measurement period Tmeas may also be concluded based on the response signal themselves. For example, a detected response signal associated with presence of functionalized particles localized at the first location (i.e., an indication of target analyte at the first location), may follow a characteristic curve, such as an initial incline in response signal followed by a more gradual trailing edge that fades into the background signal over time. In some cases, the measurement interval Tmeas may be concluded based on a trend or pattern in the response signal over time, as indicated by the sensor data. The measurement interval Tmeas may also be concluded upon detecting an indication that the response signal is sustained below a minimum threshold for a length of time, or that the average is below a threshold for a length of time.

At block 812, the sensor data obtained in block 810 can be used to determine the presence or absence of the target analyte within the first portion of the living body. For instance, the determination may involve quantifying the data indicative of the response signal during the measurement interval Tmeas, and comparing the quantified result to a threshold. The determination may therefore involve computing an average, maximum, minimum, trend, signal to noise ratio, or cumulative power of the response signal during the measurement interval and comparing that number with a threshold value. Further, the threshold value may be set in part based on one or more measured, predicted, and/or empirically derived factors related to the in vivo measurement environment, such as blood pressure, pulse rate, distance between the two locations on the body, etc. Further, the sensor data may also be used to estimate an abundance of the target analyte within the first location of the body.

Upon making the determination of the presence or absence (or abundance) of the analyte within the first location of the body, the sensor device may also generate an indication of that information, which may be displayed on a user interface of the sensor device or communicated to another server where the information can be made accessible to the wearer.

B. Example Drug Activation Detection System

Figure 9A:
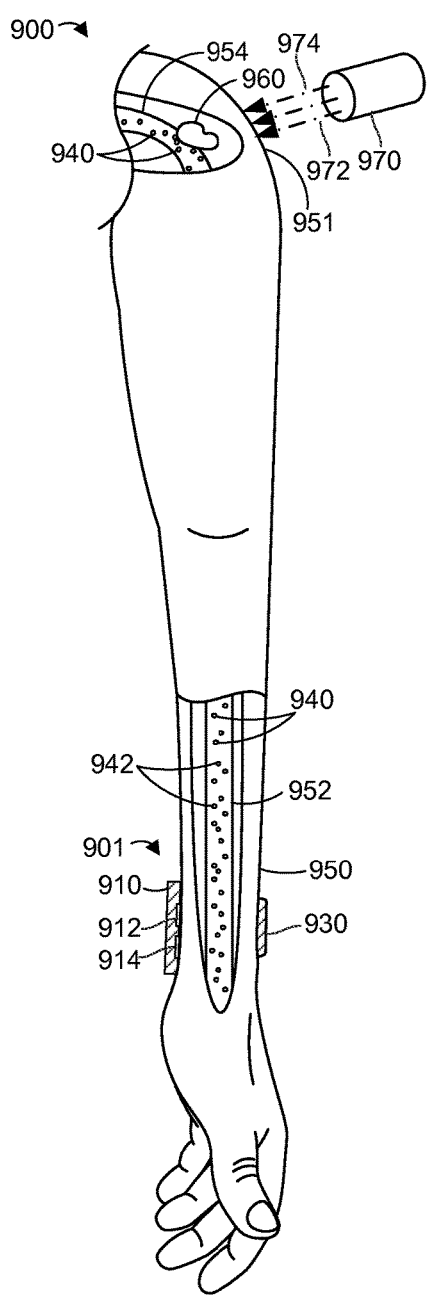
FIG. 9A is a partial cross-sectional view of a drug-delivery system used to detect an amount of drug activated within a living body.
Figure 9B:
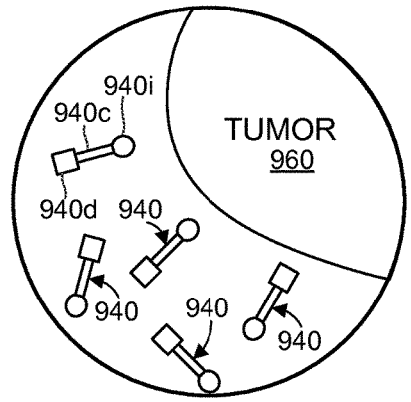
FIGS. 9B, 9C, and 9D are diagrams illustrating interaction of functionalized particles with absorbed light during a drug activation process.
Figure 9C:
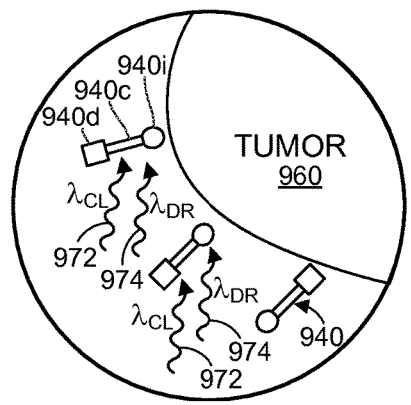
Figure 9D:
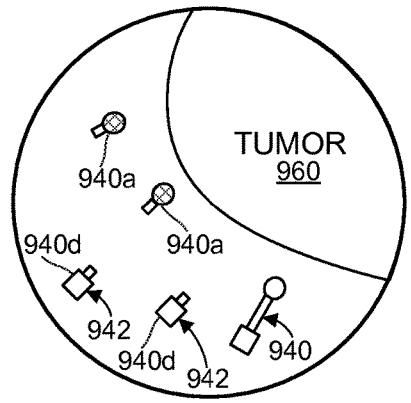

A drug activation detection system is described in connection with FIGS. 9A-9D and 10A-10C. FIG. 9A is a partial cross-sectional view of a drug activation detection system 900. FIGS. 9B, 9C, and 9D are diagrams illustrating interaction of functionalized particles with absorbed light during a drug activation process. Functionalized particles 940 are introduced into a living body (e.g., via injection, ingestion, or inhalation). The functionalized particles 940 disperse throughout the body via the circulatory system. As shown in FIG. 9A, which is a view of an arm including partial cross-sections at the shoulder 951 and forearm 950, the functionalized particles 940 are distributed throughout the subsurface vasculature 954 near the shoulder 951 and the subsurface vasculature 952 of the forearm 950. The circulatory system of the body may circulate the functionalized particles 940 through a network of lumens in the subsurface vasculature such that some functionalized particles from different parts of the living body eventually pass in proximity to a wearable sensor device 901 where the particles 940 can be interrogated. The analyte detection system 900 includes a wearable sensor device 901 mounted to a wrist, and a light source 970 arranged to emit light 972 toward the shoulder 951. A tumor 960 may be present within the shoulder 951, and some of the circulating functionalized particles 940 may become proximate to the tumor 960 via the subsurface vasculature 954 in the shoulder 951.

i. Photocleavable Functionalized Particles for Drug Delivery

The functionalized particles 940, which are shown in FIGS. 9B-9D, each include a detectable label 940*d* and a biological agent that are coupled via a photocleavable linker 940*c*. The biological agent may be drug, an ion, or another compound or substance that is initially in a biologically inactive (e.g., inert) state (940*i*). The agent may be configured to transition to a biologically active state (940*a*) upon absorbing light 974 at a drug activation wavelength λDR, as shown in FIGS. 9C and 9D.

The detectable label 940*d* may include any of the detectable labels described above in connection with FIGS. 6A-6D, including the various fluorophores that are modified in response to absorbing directed energy. As such, a stimulus may be applied to a particular region of the body (e.g., via the light source 970 at the shoulder 951), and a subsequent detection of fluorophores modified in accordance with the stimulus (e.g., via the sensor device 901 at the wrist 950) may be determined to be from fluorophores that came from the particular region of the body.

In some examples, the functionalized particles 940 may also include an analyte-selective binder that is configured to bind to one or more target analyte with a particular affinity and/or selectivity. Including an analyte-selective binder may assist in targeting and/or localizing an eventual activation of the biological agent because the functionalized particles may become localized near a target analyte associated with the region of the body in which the biological agent is desired to be activated. For instance, the functionalized particles 940 may include an analyte-selective binder that is configured to bind to the tumor 960, such as a receptor associated with a cancerous cell.

ii. Drug-Delivery System Working Principle

The light source 970 can be a light source that emits cleaving light 972 at a wavelength that includes a cleaving wavelength λCL for separating two portions of the functionalized particles 940. In particular, the light 972 can cause a detectable portion 942 of the functionalized particle 940 to separate from the biological agent portion of the functionalized particle 940, and the detectable portion 942 can then be distributed through the circulatory system separately from the analyte-selective portion of the functionalized particle 940.

The wearable sensor device 901 may be implemented as any of the sensor devices 100, 200, 300, 400, 500 described above, and can include a variety of sensors for detecting response signals indicative of a presence of functionalized particles within the subsurface vasculature 952 of the body. As shown in FIG. 9A, the sensor device 901 may include a sensor housing 910 with an emitter 912 and a detector 914. The sensor device 901 is mounted via a strap 930 such that the sensor housing 910 is situated over the anterior side of the wearer's wrist. During measurement, the emitter 912 can direct energy (e.g., an excitation light) into the subsurface vasculature 952 of the wrist, and the detector 914 can detect a response signal from the functionalized particles 940 (and detectable portions 942 of separated functionalized particles) within the subsurface vasculature 952. The detector 914 may be, for example, a photosensor that detects a fluorescent emission generated by the functionalized particles in response to the interrogating signal from the emitter 912. The sensor device 901 may further be configured to distinguish between functionalized particles 940 which have not been photocleaved (e.g., from detectable labels 940*d* included in a functionalized particle 940), and detectable portions 942, which have been photocleaved from the biological agent (e.g., from detectable labels 940*d* included in a detectable portion 942).

The functionalized particles 940 circulate through the body. Over time, some of the dispersed functionalized particles 940 may be present near the tumor 960 in the shoulder 951. The light source 970 is then used to emit both drug activation light 974, at wavelength λDR, and cleaving light 972 toward the shoulder area 951, as shown in FIG. 9C. The drug activation light 974 is absorbed by the biological agent and causes the agent to transition from a biologically inactive state (940*i*) to a biologically active state (940*a*). Because the biological agent transitions to the active state 940*a* near the tumor 960, the biological agent may engage the tumor 960 in a relatively localized, targeted way. The cleaving light 972 cleaves at least some of the photocleavable linkers 940*c* that were bound to the tumor 960. As shown in FIG. 9D, the cleaving light 972 separates the functionalized particles 940 into a portion that includes the biological agent and a detectable portion 942 that includes the detectable label 940*d*.

Upon applying the cleaving light 972, a number of detectable portions 942 continue to traverse the circulatory system of the body, where they may be eventually detected by the sensor device 701. Thus, the application of the cleaving light 972 and drug activation light 974 via the light source 970 at a given location of the body may be used as a probe to test for the amount of drug that transitioned to the active state at that location, and thus the amount of drug that was effectively delivered at that location. If the sensor device 901 detects an increase in the response signal due to the detectable portions 942 during some measurement interval that follows application of the cleaving light 972, it may be concluded that some of the functionalized particles 940 transitioned to a biologically active state in the region where the cleaving light 972 and drug activation light 974 was applied.

iii. Example Operation of the Drug Activation Detection System

Figure 10A:
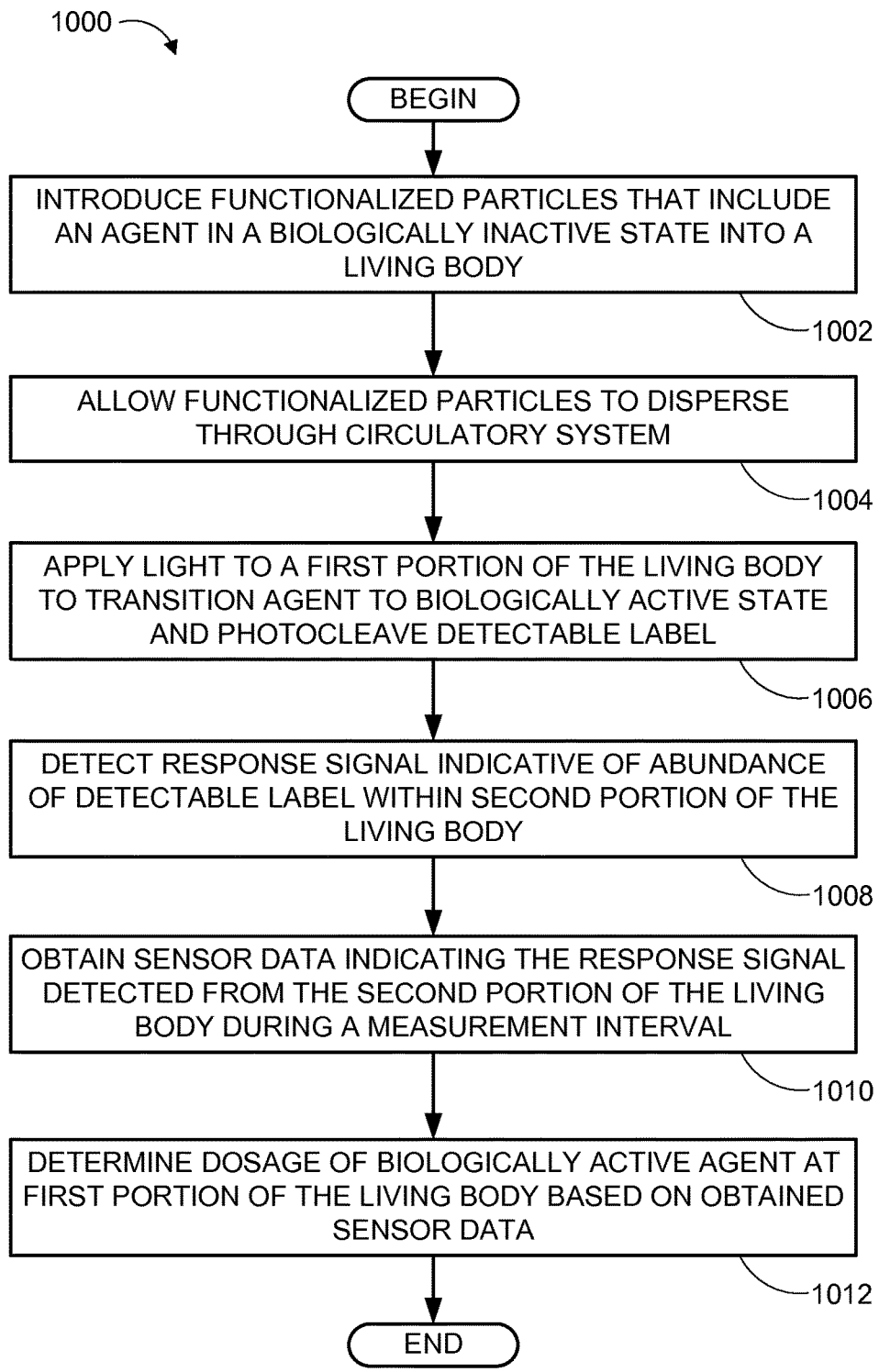
FIG. 10A is a flowchart of an example process for operating a drug-delivery system.
Figure 10B:
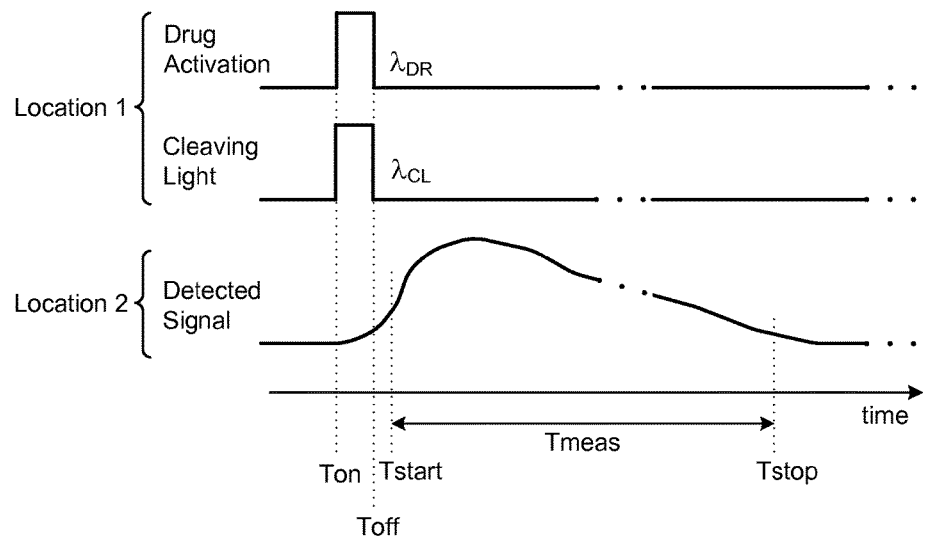
FIGS. 10B and 10C are timing diagrams illustrating operation of the light source(s) and detected response signals during a drug activation process.
Figure 10C:
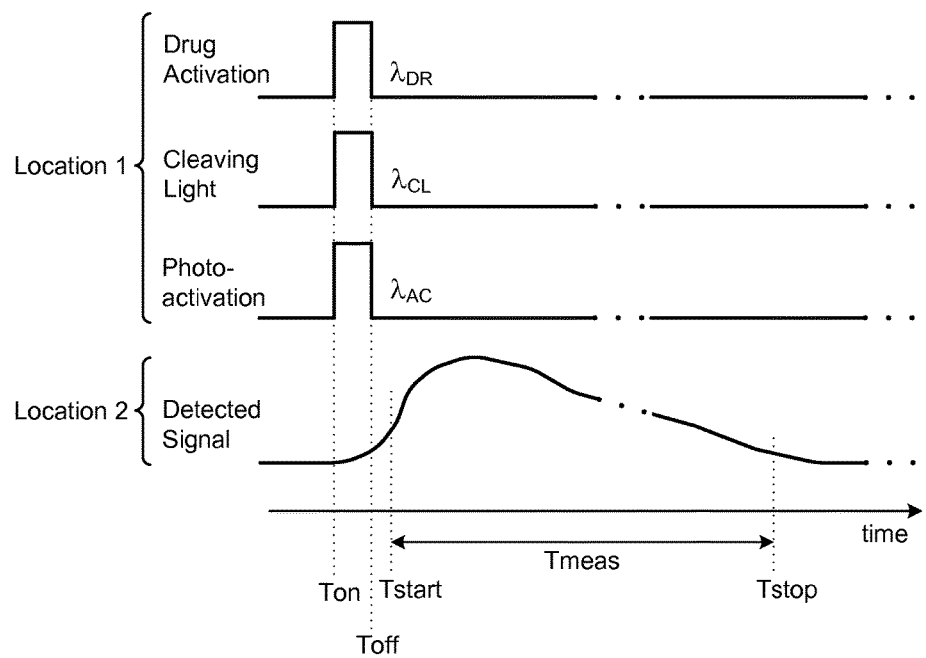

FIG. 10A is a flowchart of an example process 1000 for operating a drug activation detection system, such as the drug activation detection system 900. FIGS. 10B and 10C are timing diagrams illustrating operation of the light source(s) and detected response signals during an analyte measurement process. The following description of the process 1000 references the timing diagrams of FIGS. 10B-10C and also the example system 900 shown in FIGS. 9A-9D.

At block 1002, functionalized particles that include an agent in a biologically inactive state are introduced into a living body. As noted above, the functionalized particles may be introduced by injection, inhalation, ingestion, etc. The functionalized particles can include any number of biologically inactive agents, such as drugs, ions, or another molecular payload configured to interact with a biological environment in response to receiving an activating stimulus. In addition, the biologically inactive agent is coupled to a detectable label through a photocleavable binder. For example, the functionalized particles 940 include the detectable label 940d coupled to the inactive biological agent 940i through the photocleavable binder 940c.

At block 1004, the functionalized particles introduced in block 1002 are allowed to disperse through the circulatory system of the body. In some cases, the functionalized particles may become immobilized or otherwise localized near particular target analytes as they disperse through the circulatory system. As noted above, the speed at which the functionalized particles are dispersed through the circulatory system may depend in part on a number of factors of the particles themselves, including the size, materials, etc., as well as factors related to the in vivo environment of the living body (e.g., blood pressure, density of target analytes encountered, etc.). Thus, the duration of the time for which the functionalized particles are allowed to disperse may be based in part on a number of measured parameters, predictions, and/or empirical results.

At block 1006, light is applied to a first portion of the living body to transition the biologically inactive agent to a biologically active state and to photocleave the detectable label from the biological agent. For example, as shown in FIGS. 9B-9D, application of the drug activation light 974 and the cleaving light 972 causes the functionalized particle 940 to separate into the detectable portion 942 and a portion that includes the active biological agent 940*a*. The photocleaving light can be applied at a particular wavelength and for a particular duration, which each may depend on the particular photocleavable linker being used. Similarly, the drug activation light can be applied at a particular wavelength and for a particular duration, which each may depend on the particular biological agent being used. In addition, the applied light may be selected in accordance with one or more safety parameters so as to, for example, limit an energy dosage of radiation applied to a given area and/or volume of the living body. The application of the drug activation light at wavelength λDR and photocleaving light at wavelength λCL to the first location of the body is shown in FIG. 10B, in which the light is applied for a duration that spans from an initial time Ton to an end time Toff. Of course, depending on a particular implementation, the light may be applied in other manners as well, such as an example in which the power of the cleaving light during application is non-continuous.

In addition, as shown in FIG. 10C, an activation light, or another stimulus to modify a detectable response signal of the detectable label 940*d*, may be also be applied to the first location of the body at or near the time of application of the drug activation light and the photocleaving light. As described in connection with FIG. 6C, the activation light at an activation wavelength λAC can cause the response signal from the detectable label to be modified, and therefore distinguishable from detectable labels that have not been exposed to the activation light. In another example, the detectable label 940*d* may be a photoswitchable fluorophore as described in connection with FIG. 6D, in which case a switching light at a switching wavelength λSW may be applied at or near the same time as the cleaving light. In some cases, the light source 970 may emit light that includes light at both the drug-activation wavelength λDR, the cleaving wavelength λCL, and the activation wavelength λAC (or switching wavelength λSW) such that the functionalized particles 940 may be transitioned to a biologically active state, cleaved, and their response signal modified simultaneously. In some cases, photoactivation (or photoswitching) of the detectable label 940*d* may be induced by light at an activation wavelength λAC (or switching wavelength λSW) that is near to (or the same as) the cleaving wavelength λCL and/or the drug-activation wavelength λDR.

At block 1008, a response signal is detected that is indicative of an abundance of the detectable label within a second portion of the body. For example, the wearable sensor device 901 may be used to detect the presence of the detectable label 940*d* on the functionalized particles and/or the detectable portions 942 of cleaved particles within the vasculature 952 of the forearm 950. The sensor device 901 may emit an excitation signal into the subsurface vasculature 952 via the emitter 912, and then detect a fluorescent response signal using the detector 914.

In an example in which the detectable labels 940*d* in the first portion of the living body were modified via activation light, as in FIG. 10C, the sensor device 901 may be configured to distinguish between response signals from the cleaved detectable portion 942 and the uncleaved functionalized particles 940. In some cases, the sensor device 901 may detect response signals preferentially from the cleaved detectable portions 942. For instance, if the detectable labels are photoswitchable fluorophore or a photoactivated fluorophore, and switching or activating light was applied to the first location of the body near the time of the cleaving light, then the sensor device 901 may emit an interrogating light and/or detect a responsive fluorescent light that corresponds only to the modified version of the fluorophore.

At block 1010, sensor data that indicates the response signal detected from the second portion of the body during a measurement interval is obtained using the sensor device. As shown in FIGS. 10B-10C, the measurement interval can be a period of time that begins at a start time Tstart, lasts for period Tmeas, and ends at a stop time Tstop. The start time may have a relationship with the time(s) at which the cleaving light is applied (i.e., Ton and/or Toff). For example, the start time Tstart may begin at a time at which detectable portions 942 of cleaved functionalized particles are expected to disperse from the shoulder 951, where they were near the tumor 960, to the wrist 950, where their presence can be detected via the sensor device 901. Thus, Tstart may be selected based in part on measured, predicted, and/or empirically derived factors, such as blood pressure, pulse rate, distance between the first and second locations of the living body, through the circulatory system, among other factors. Similarly, the duration Tmeas of the measurement interval can also be selected based on a variety of factors related to an expected period in which detectable portions 942 of cleaved functionalized particles are expected to disperse from the shoulder 951 to the wrist 950. In some cases, the measurement period Tmeas may also be concluded based on the response signal themselves. For example, a detected response signal associated with presence of functionalized particles localized at the first location (i.e., an indication of target analyte at the first location), may follow a characteristic curve, such as an initial incline in response signal followed by a more gradual trailing edge that fades into the background signal over time. In some cases, the measurement interval Tmeas may be concluded based on a trend or pattern in the response signal over time, as indicated by the sensor data. The measurement interval Tmeas may also be concluded upon detecting an indication that the response signal is sustained below a minimum threshold for a length of time, or that the average is below a threshold for a length of time.

At block 1012, the sensor data obtained in block 1010 can be used to determine the dosage of the biologically active agent at the first portion of the living body. For instance, the determination may involve quantifying the data indicative of the response signal during the measurement interval Tmeas, and comparing the quantified result to a threshold.

Upon making the determination of the abundance of the dosage of the biological agent activated at the first location of the body, the sensor device may also generate an indication of that information, which may be displayed on a user interface of the sensor device or communicated to another server where the information can be made accessible to the wearer.

C. Additional Embodiments

In some examples, functionalized particles may include two portions that are coupled via a cleavable linker that can be cleaved by a stimulus other than absorbing light. For example, some embodiments may include linkers that can be cleaved by application of directed energy in the form of ultrasound waves. Such systems may therefore include an ultrasound generator or another acoustic energy delivery system that can apply directed acoustic waves into a particular location of a body so as to cleave the cleavable linkers of the functionalized particles in that region of the body. Upon cleaving, a detectable label can be separated from the functionalized particle and circulate to another location of the body where it can be detected via a sensor device at the other location of the body.

In some examples, a single apparatus be configured to obtain measurements indicative of the presence of functionalized particles (e.g., fluorescence measurements) and to provide directed energy into the body. For example, some implementations may use a wand apparatus or another portable and/or handheld device that includes both a directed energy source (e.g., laser light source) for providing a stimulus to functionalized particles in vivo (e.g., to cleave the particles and/or induce a modification in a detectable signature of a detectable label), and a sensor platform that is configured to detect a presence of the functionalized particles within the body. Such an apparatus may be configured to be placed along or near an exterior of a living body, or inserted into a cavity of the body. A particular form factor may be selected in part based on a type of tissue at which drug activation is being effected. For instance, a drug delivery system or analyte detection system associated with prostate cancer may involve an apparatus configured for rectal insertion. Such an apparatus may further include additional sensors for obtaining diagnostically relevant information, such as ultrasound sensors and/or photoacoustic sensors. An example of a single apparatus with this configuration is described, by way of example, in connection with FIG. 11B.

V. Example Systems

Figure 11A:
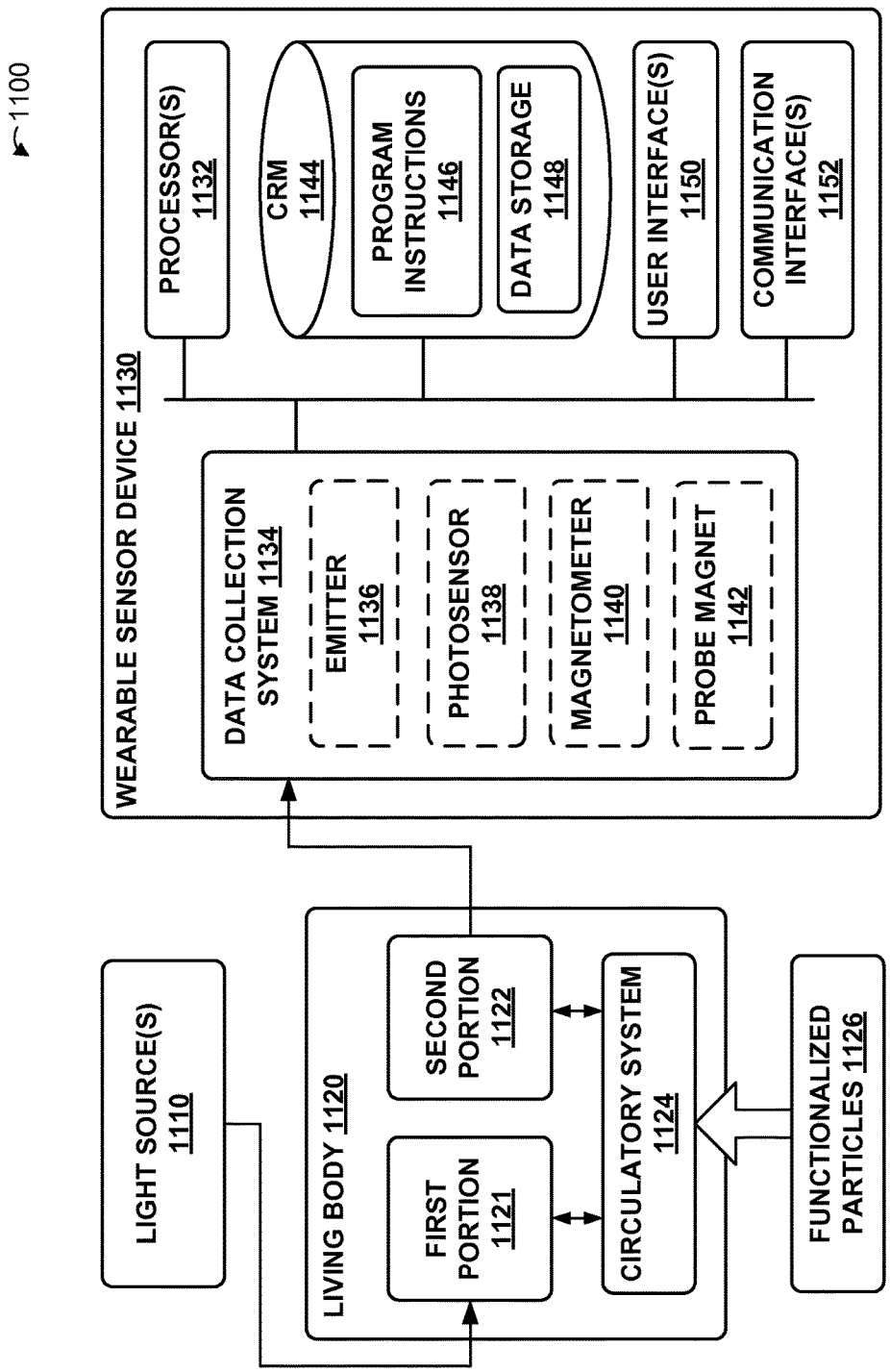
FIG. 11A is a functional block diagram of an example system including a wearable sensor device.
Figure 11B:
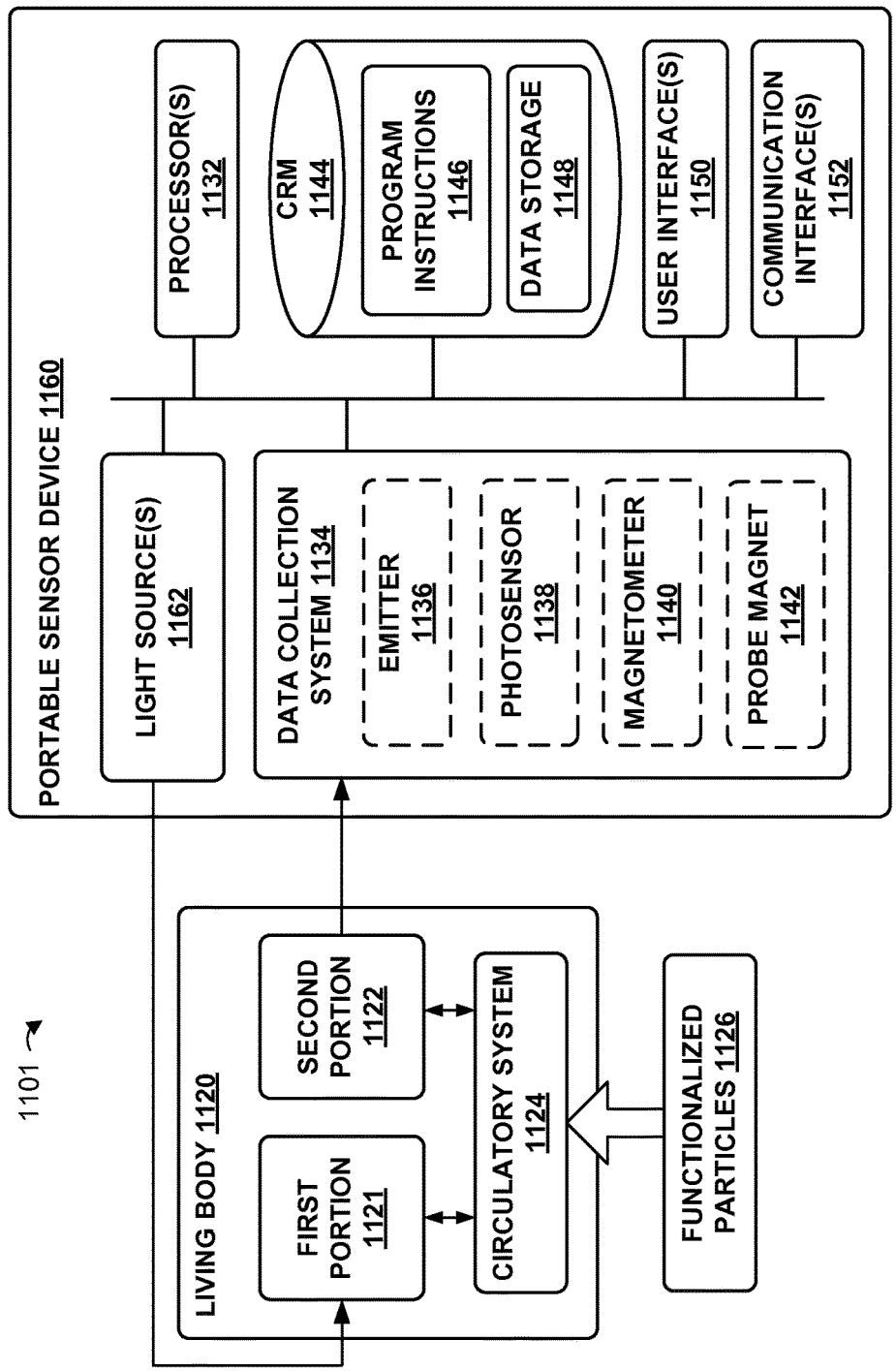
FIG. 11B is a functional block diagram of an example system including a portable sensor device.

FIG. 11A is a functional block diagram of an example systems 1100 including a wearable sensor device 1130 (e.g., a wrist-mountable device). FIG. 11B is a functional block diagram of an example system 1101 including a portable sensor device 1160 (e.g., a wand-type device). Either of the systems 1100, 1101 may be used to perform the analyte detection operations and/or drug activation detection operations described above.

The system 1100 includes a wearable sensor device 1130 and one or more light sources 1110. A living body 1120 includes a first portion 1121 and a second portion 1122 that are each served by a circulatory system 1124. Functionalized particles 1126 are introduced into the living body 1120, where they are dispersed throughout by the circulatory system 1124 such that at least some reach the first portion 1121 and the second portion 1122. The functionalized particles 1126 can include a detectable label that is coupled to another functional group via a photocleavable linker or spacer. The functional group may be an analyte-selective binder or an agent configured to transition from a biologically inactive state to a biologically active state.

The light source 1110 is configured to emit stimulating light into the first portion 1121. The stimulating light may include, for example, drug activation light, photocleaving light, and/or light that modifies a response signal of the detectable label, such as photoactivating light, photoswitching light, photoconverting light, etc. Thus, the stimulating light emitted into the first portion may cleave a detectable label from functionalized particles in the first portion 1121 and may activate a biological agent thereof, for example. Upon emitting stimulating light into the first portion 1121, the detectable labels that are cleaved from the functionalized particles disperse through the circulatory system 1124 and at least some of those reach the second portion 1122 of the body.

The wearable sensor device 1130 is situated to detect response signals from functionalized particles in the second portion 1122 of the body. For example, the wearable sensor device 1130 may be a wrist-mountable device and the second portion 1122 of the body may be a wrist. Wearable device 1130 may take the form of or be similar to one of the wrist-mounted devices 100, 200, 300, 400, 500, shown in FIGS. 1A-1B, 2A-2B, 3A-3B, 4A-4B, 5A-5B. However, wearable device 1130 may also take other forms, such as an ankle, waist, or chest-mounted device.

The wearable sensor device 1130 includes a data collection system 1134, one or more processors 1132, a computer readable medium 1144, user interfaces 1150, and communication interfaces 1152. The components of the wearable device 1130 may be disposed on a mount for mounting the device to an external body surface where a portion of subsurface vasculature of the second portion 1122 of the body 1120 is readily observable.

Processor 1132 may be a general-purpose processor or a special purpose processor (e.g., digital signal processors, application specific integrated circuits, etc.). The one or more processors 1132 can be configured to execute computer-readable program instructions 1146 that are stored in the computer readable medium 1144 and are executable to provide the functionality of a wearable device 1130 described herein.

The computer readable medium 1144 may include or take the form of one or more non-transitory, computer-readable storage media that can be read or accessed by at least one processor 1132. The one or more computer-readable storage media can include volatile and/or non-volatile storage components, such as optical, magnetic, organic or other memory or disc storage, which can be integrated in whole or in part with at least one of the one or more processors 1132. In some embodiments, the computer readable medium 1132 can be implemented using a single physical device (e.g., one optical, magnetic, organic or other memory or disc storage unit), while in other embodiments, the computer readable medium 1144 can be implemented using two or more physical devices.

Data collection system 1134 may include an emitter 1136 and a detector 1138. In some embodiments, the data collection system 1134 may additionally or alternatively include a magnetometer 1140 and a probe magnet 1142. As described above, the data collection system 1134 may include any detector capable of detecting at least one physiological parameter, which could include any parameters that may relate to the health of the person wearing the wearable device. For example, the photosensor 1138 could be configured to measure a fluorescent response signal generated by detectable labels in the second portion 1122 of the body in response to an excitation signal from the emitter 1136. In some examples, the data collection system 1134 could measure a magnetic field strength indicative of a presence of magnetic and/or paramagnetic materials within the second portion 1122 of the body by, for example, applying a magnetic field using the probe magnet 1142 and detecting the resulting field strength via the magnetometer 1140. Differences from an expected magnetic field strength may be due to the presence of paramagnetic materials within functionalized particles in the second portion 1122 of the living body 1120. The data collection system 1134 may also include sensors for blood pressure, pulse rate, skin temperature, etc. In some examples, the data collection system 1134 includes detectors, such as photosensor 1138, which may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. Further, the data collection system 1134 can include a signal source, such as emitter 1136, which is configured to generate an interrogating signal that can penetrate the wearer's skin into the subsurface vasculature of the second portion 1122 so as to stimulate detectable labels therein to generate a response signal. In general, the signal source may generate an interrogation signal that will produce a responsive signal that can be detected by one or more of detectors. The interrogating signal can be any kind of signal that is benign to the wearer, such as electromagnetic, magnetic, optic, acoustic, thermal, mechanical, and results in a response signal that can be used to measure a physiological parameter.

The program instructions 1146 stored on the computer readable medium 1144 may include instructions to perform or facilitate some or all of the device functionality described herein. The program instructions 1146 may include instructions for operating the data collection system 1134. For example, there may be instructions for controlling the emitter 1136 to transmit an interrogating signal at preset measurement times and controlling the photosensor 1138 to receive data representative of response signals transmitted from the portion of subsurface vasculature in response to the interrogating signals transmitted at the preset measurement times.

The program instructions 1146 may also include instructions for operating the user interface 1150. For example, there may be instructions for displaying data collected by the data collection system 1134 and analyzed by the calculation and decision module, or for displaying one or more alerts generated by an alert module. Further, there may be instructions to execute certain functions based on inputs accepted by the user interface 1150, such as inputs accepted by one or more buttons disposed on the user interface.

Communication interface 1152 may also be operated by instructions within the program instructions 1146, such as instructions for sending and/or receiving information via a wireless antenna, which may be disposed on or in the wearable device 1130. The communication interface 1152 can optionally include one or more oscillators, mixers, frequency injectors, etc. to modulate and/or demodulate information on a carrier frequency to be transmitted and/or received by the antenna. In some examples, the wearable device 1130 is configured to indicate an output from the processor by modulating an impedance of the antenna in a manner that is perceivable by a remote server or other remote computing device.

The program instructions may include a calculation and decision module that includes instructions for receiving data from the data collection system 1134 in the form of a responsive signal, analyzing the data to determine if the target analyte is present or absent, quantify the measured physiological parameter(s), such as presence of a target analyte, or dosage of an activated biological agent, and analyzing the data to determine if a medical condition is indicated. For instance, the calculation and decision module may include instructions for determining, for each preset measurement time, a presence and/or concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module may, in some examples, be stored in a computer-readable medium and executed by a processor located external to the wearable device. For example, the wearable device 1130 could be configured to collect certain data regarding physiological parameters from the wearer and then transmit the data to a remote server, which may include a mobile device, a personal computer, the cloud, or any other remote system, for further processing.

The computer readable medium 1144 may further contain other data 1148 or information, such as medical and health history of the wearer of the device or calibration information for the data collection system 1134, which may be useful in determining whether a medical condition is indicated. Further, the computer readable medium 1144 may contain data corresponding to certain analyte baselines, above or below which a medical condition is indicated. The baselines may be pre-stored on the computer readable medium 1155, may be transmitted from a remote source, such as a remote server, or may be generated by the calculation and decision module itself. The calculation and decision module may include instructions for generating individual baselines for the wearer of the device based on data collected over a certain number of measurement periods. For example, the calculation and decision module may generate a baseline concentration of a target blood analyte for each of a plurality of measurement periods by averaging the analyte concentration at each of the measurement periods measured over the course of a few days, and store those baseline concentrations in the data storage 1148 for later comparison. Baselines may also be generated by a remote server and transmitted to the wearable device 1130 via communication interface 1152. The calculation and decision module may also, upon determining that a medical condition is indicated, generate one or more recommendations for the wearer of the device based, at least in part, on consultation of a clinical protocol. Such recommendations may alternatively be generated by the remote server and transmitted to the wearable device 1130.

In response to a determination by the calculation and decision module that a medical condition is indicated, an alert may be provided via the user interface 1150. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Referring now to FIG. 11B, the system 1101 includes a portable sensor device 1160. The portable sensor device 1160 includes a light source 1162 for emitting stimulating light into the first portion 1121 and the data collection system 1134 described above, which is configured to detect response signals from the second portion 1122 of the body 1120. Functionalized particles 1126 are introduced into the living body 1120, where they are dispersed throughout by the circulatory system 1124 such that at least some reach the first portion 1121 and the second portion 1122.

The light source 1162 is configured to emit stimulating light into the first portion 1121. The stimulating light may include, for example, drug activation light, photocleaving light, and/or light that modifies a response signal of the detectable label, such as photoactivating light, photoswitching light, photoconverting light, etc. Thus, the stimulating light emitted into the first portion may cleave a detectable label from functionalized particles in the first portion 1121 and may activate a biological agent thereof, for example. Upon emitting stimulating light into the first portion 1121, the detectable labels that are cleaved from the functionalized particles disperse through the circulatory system 1124 and at least some of those reach the second portion 1122 of the body.

The portable sensor device 1160 can be positioned along or near an exterior portion of the body 1120 such that the data collection system can detect response signals from functionalized particles in the second portion 1122 of the body 1120. For example, the portable sensor device 1160 may be a wand or another handheld device that includes the light source 1162 and the data collection system 1134 in a single housing. The housing of the portable sensor device 1160 may be configured for placement near an exterior surface of the body and may include deformable and/or flexible regions to facilitate placement of the sensor-containing regions of the device 1160. In some examples, the portable sensor device 1160 may be implemented as an insertable device, such as in applications in which analyte detection and/or biological agent activation is desired to be detected in a region that is most readily accessible from a body cavity, such as a rectal cavity, for example.

In the system 1101, the spatial separation between the first portion 1121 and the second portion 1122 of the living body 1120 is set based on the physical arrangement of the light source 1162 and the data collection system 1134 in the portable sensor device 1160. Generally, because the portable sensor device 1160 may be placed adjacent, near, or within a range of different location of the body, the data collection system 1134 may be situated much closer to the light source 1162 in system 1101 than the light source 1110 in system 1100. For example, the light source 1162 and data collection system 1134 may be arranged with respect to one another such that the second portion 1122 of the living body may be a lumen of the subsurface vasculature, and the first portion 1121 may be tissue proximate that lumen. In some cases, the first portion 1121, at which the stimulating light is applied from the light source 1162, may at least partially overlap with the second portion, at which cleaved detectable labels can be detected (e.g., adjacent and/or overlapping sections of tissue and/or vasculature).

Therefore, the distance for detectable labels cleaved in the first portion 1121 to traverse through the circulator system 1124 before being detectable in the second portion 1122 may be much less in the system 1101 than in the system 1100. The system 1101 may therefore allow for detections of cleaved detectable labels with less lag time and with greater signal strength compared to approaches using a wearable sensor device with a fixed sensor location.

Figure 12:
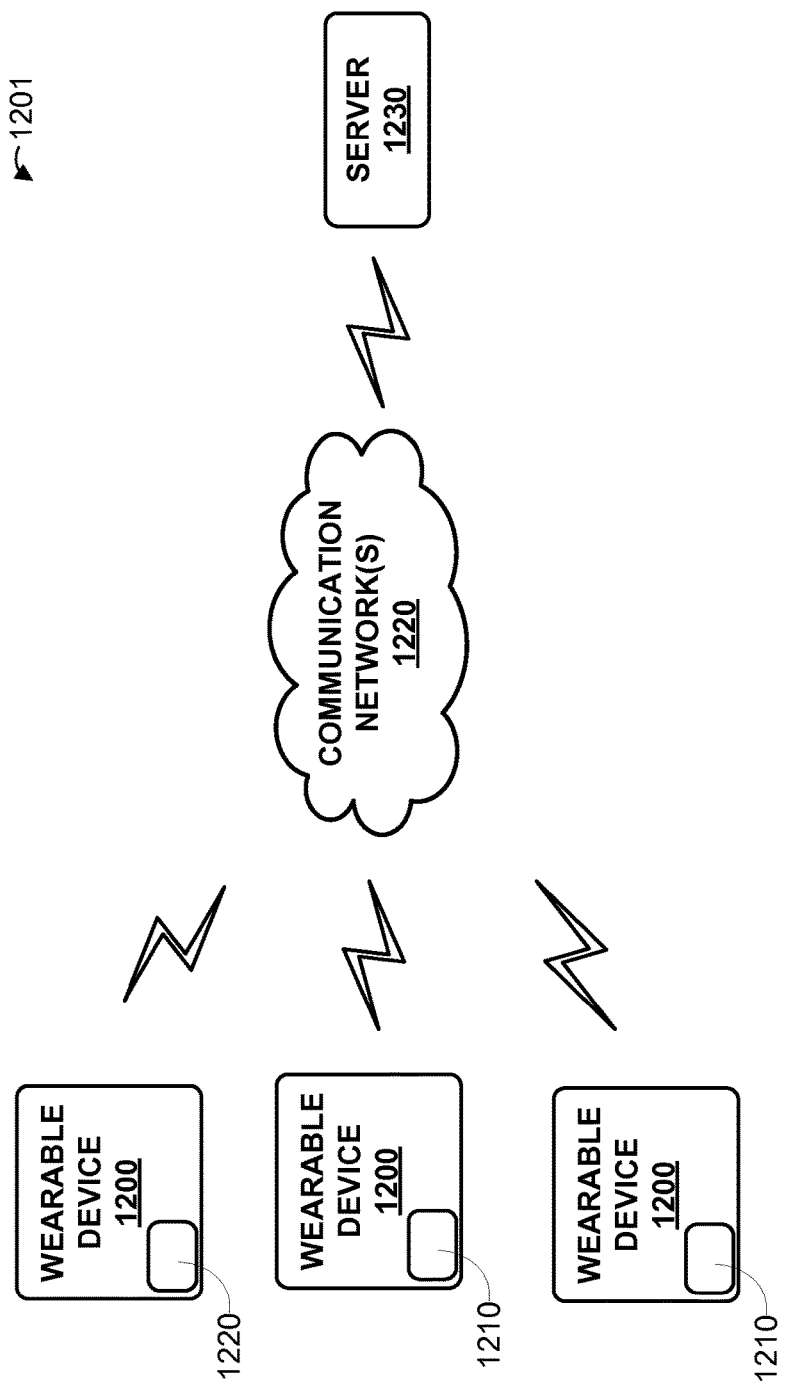
FIG. 12 is a block diagram of an example system that includes multiple wearable devices in communication with a server.

FIG. 12 is a simplified schematic of a system including one or more wearable devices 1200. The one or more wearable devices 1200 may be configured to transmit data via a communication interface 1210 over one or more communication networks 1220 to a remote server 1230. In one embodiment, the communication interface 1210 includes a wireless transceiver for sending and receiving communications to and from the server 1230. In further embodiments, the communication interface 1210 may include any means for the transfer of data, including both wired and wireless communications. For example, the communication interface may include a universal serial bus (USB) interface or a secure digital (SD) card interface. Communication networks 1220 may be any one of may be one of: a plain old telephone service (POTS) network, a cellular network, a fiber network and a data network. The server 1230 may include any type of remote computing device or remote cloud computing network. Further, communication network 1220 may include one or more intermediaries, including, for example wherein the wearable device 1200 transmits data to a mobile phone or other personal computing device, which in turn transmits the data to the server 1230.

In addition to receiving communications from the wearable device 1200, such as collected physiological parameter data and data regarding health state as input by the user, the server may also be configured to gather and/or receive either from the wearable device 1200 or from some other source, information regarding a wearer's overall medical history, environmental factors and geographical data. For example, a user account may be established on the server for every wearer that contains the wearer's medical history. Moreover, in some examples, the server 1230 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

VI. Conclusion

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A system comprising:
   one or more light sources configured to emit light including light at a first wavelength into a first portion of a living body that has received a plurality of functionalized particles, the functionalized particles each comprising a first portion coupled to a second portion via a photocleavable linker, wherein the first portion comprises a detectable label, wherein the second portion is configured to specifically bind to a target analyte, and wherein the photocleavable linker is configured to undergo a reaction that separates the first portion from the second portion responsive to absorption of light at the first wavelength;
   a sensor device configured to detect a response signal from a second portion of the living body, wherein the first portion of the living body is different from the second portion of the living body, and wherein the response signal is indicative of an abundance of the detectable label in the second portion of the living body; and
   a control system configured to: (i) following an emission of light at the first wavelength into the first portion of the living body by the one or more light sources, use the sensor device to obtain sensor data indicative of the response signal from the second portion of the living body detected by the sensor device during a measurement interval, wherein the measurement interval is based at least in part on a distance between the first portion of the living body and the second portion of the living body, and (ii) determine a presence or absence of the target analyte within the first portion of the living body based in part on the obtained data.

2. The system of claim 1, wherein the detectable label comprises a fluorophore configured to emit light at a fluorescence wavelength responsive to absorption of light at an excitation wavelength, and wherein the sensor device comprises (i) an emitter configured to emit light at the excitation wavelength into the second portion of the living body and (ii) a photosensor configured to detect light at the fluorescence wavelength emitted from the second portion of the living body.

3. The system of claim 1, wherein the control system is further configured to, beginning at an initial time and for a predetermined duration, cause the light source to emit light into the first portion of the living body, wherein the measurement interval has a predetermined start time and a predetermined stop time relative to the initial time.

4. The system of claim 1, wherein the detectable label comprises a photoactivated dye configured to, responsive to absorption of light at a second wavelength emitted by the one or more light sources, transition from a low fluorescence state to a high fluorescence state in which the detectable label is configured to emit light at a fluorescence wavelength responsive to absorption of excitation light at an excitation wavelength, and
   wherein the sensor device comprises (i) an emitter configured to emit light at the excitation wavelength into the second portion of the living body and (ii) a photosensor configured to detect light at the fluorescence wavelength emitted from the second portion of the living body.

5. The system of claim 1, wherein the detectable label comprises a photoswitchable dye configured to: (i) responsive to absorption of light at a second wavelength emitted by the one or more light sources, transition from a first fluorescence state to a second fluorescence state, (ii) while in the first fluorescence state, emit light at a first fluorescence wavelength responsive to absorption of light at a first excitation wavelength, and (iii) while in the second fluorescence state, emit light at a second fluorescence wavelength responsive to absorption of light at a second excitation wavelength, wherein the first fluorescence wavelength is different from the second fluorescence wavelength, and wherein the sensor device comprises: (i) an emitter configured to emit light at the second excitation wavelength into the second portion of the living body and (ii) a photosensor configured to detect light at the second fluorescence wavelength emitted from the second portion of the living body.

6. The system of claim 1, wherein the detectable label comprises a magnetic or paramagnetic material, and wherein the sensor device comprises a magnetometer configured to detect the response signal based on a magnetic interaction between the magnetometer and the magnetic or paramagnetic material within the second portion of the living body.

7. The system of claim 1, wherein the abundance of detectable labels indicated by the response signal comprises a first subset of detectable labels, which are included in first portions of the functionalized particles that have been separated from respective second portions thereof, and a second subset of detectable labels, which are included in unseparated functionalized particles, and wherein the control system is configured to estimate an abundance of the first subset of detectable labels in the second portion of the living body based on a comparison between sensor data obtained during the measurement interval and baseline data relating to a measured proportion of unseparated functionalized particles.

8. The system of claim 1, wherein the second portion of each of the functionalized particles comprises an aptamer having a predetermined binding affinity to a receptor associated with a cancerous cell within the living body.

9. The system of claim 1, wherein the sensor device comprises a wearable device.

10. The system of claim 9, wherein the wearable device comprises a wrist-mountable device.

11. The system of claim 1, wherein the sensor device comprises a portable device configured to be placed along an exterior of the living body or inserted into a cavity of the living body.

12. A method comprising:
introducing a plurality of functionalized particles into a living body, the functionalized particles each comprising a first portion coupled to a second portion via a photocleavable linker, wherein the first portion comprises a detectable label, wherein the second portion is configured to specifically bind to a target analyte, and wherein the photocleavable linker is configured to undergo a reaction that separates the first portion from the second portion responsive to absorption of light at a first wavelength;
emitting light into a first portion of the living body via one or more light sources, wherein the emitted light includes light at the first wavelength;
following emitting the light, using a sensor device to obtain sensor data indicative of a response signal from a second portion of the living body detected by the sensor device during a measurement interval, wherein the first portion of the living body is different from the second portion of the living body, wherein the measurement interval is based at least in part on a distance between the first portion of the living body and the second portion of the living body, and wherein the response signal is indicative of an abundance of the detectable label in the second portion of the living body; and
determining a presence or absence of the target analyte within the first portion of the living body based in part on the obtained sensor data.

13. The method of claim 12, wherein the abundance of detectable labels indicated by the response signal comprises a first subset of detectable labels, which are included in first portions of the functionalized particles that have been separated from respective second portions thereof, and a second subset of detectable labels, which are included in unseparated functionalized particles, and wherein determining the presence or absence of the target analyte comprises: (i) making a comparison between sensor data obtained during the measurement interval and baseline data relating to a measured proportion of unseparated functionalized particles, (ii) estimating an abundance of the first subset of detectable labels in the second portion of the living body based on the comparison, and (iii) determining that the target analyte is present, or absent, within the first portion of the living body based on the estimated abundance of the first subset of detectable labels relative to a threshold.

14. The method of claim 12, wherein emitting light into a first portion of the living body via one or more light sources comprises, beginning at an initial time and for a predetermined duration, cause the one or more light source to emit light into the first portion of the living body, and wherein the measurement interval has a predetermined start time and a predetermined stop time relative to the initial time.

15. The method of claim 12, wherein the detectable label comprises a photoactivated dye configured to, responsive to absorption of light at a second wavelength, transition from a low fluorescence state to a high fluorescence state in which the detectable label is configured to emit light at a fluorescence wavelength responsive to absorption of excitation light at an excitation wavelength, and wherein using the sensor device to obtain the sensor data comprises: (i) the sensor device emitting light at the excitation wavelength into the second portion of the living body and (ii) the sensor device detecting light at the fluorescence wavelength emitted from the second portion of the living body.

16. A drug-delivery system comprising:
one or more light sources configured to emit light into a first portion of a living body, wherein the emitted light includes light at a first wavelength and light at a second wavelength, wherein the first wavelength is different than the second wavelength, wherein the living body has received a plurality of functionalized particles, the functionalized particles each comprising a first portion coupled to a second portion via a photocleavable linker, wherein the first portion comprises a detectable label, wherein the second portion comprises an agent configured to transition from a biologically inactive state to a biologically active state responsive to absorption of light at the first wavelength, and wherein the photo-cleavable linker is configured to undergo a reaction that separates the first portion from the second portion responsive to absorption of light at the second wavelength;
a sensor device configured to detect a response signal from a second portion of the living body, wherein the first portion of the living body is different from the second portion of the living body, and wherein the response signal is indicative of an abundance of the detectable label in the second portion of the living body; and
a control system configured to: (i) following an emission by the one or more light sources of light at the first wavelength into the first portion of the living body, use the sensor device to obtain sensor data indicative of the response signal from the second portion of the living body detected by the sensor device during a measurement interval, wherein the measurement interval is based at least in part on a distance between the first portion of the living body and the second portion of the living body, and (ii) determine an abundance of the agent that transitioned to the biologically active state in the first portion of the living body based in part on the obtained sensor data.

17. The drug-delivery system of claim 16, wherein the control system is further configured to, beginning at an initial time and for a predetermined duration, cause the light source to emit the light at the first wavelength into the first portion of the living body, wherein the measurement interval has a predetermined start time and a predetermined stop time relative to the initial time.

18. The drug-delivery system of claim 16, wherein the detectable label comprises a photoactivated dye configured to, responsive to absorption of light at a second wavelength, transition from a low fluorescence state to a high fluorescence state in which the detectable label is configured to emit light at a fluorescence wavelength responsive to absorption of excitation light at an excitation wavelength, and
wherein the sensor device is further configured to emit light at the excitation wavelength of the detectable label, and wherein using the sensor device to obtain the sensor data comprises: (i) the sensor device emitting light at the excitation wavelength into the second portion of the living body and (ii) the sensor device detecting light at the fluorescence wavelength emitted from the second portion of the living body.

* * * * *